(12) United States Patent
Wang et al.

(10) Patent No.: US 9,376,485 B2
(45) Date of Patent: Jun. 28, 2016

(54) NEUTRALIZING ANTIBODY FOR EPSTEIN BARR VIRUS-ASSOCIATED DISEASE

(71) Applicant: THE BRIGHAM AND WOMEN'S HOSPITAL, INC., Boston, MA (US)

(72) Inventors: Frederick C. S. Wang, Chestnut Hill, MA (US); Mark H. Fogg, Newton, MA (US)

(73) Assignee: The Brigham and Women's Hospital, Inc., Boston, MA (US)

(*) Notice: Subject to any disclaimer, the term of this patent is extended or adjusted under 35 U.S.C. 154(b) by 0 days.

(21) Appl. No.: 14/380,978

(22) PCT Filed: Feb. 27, 2013

(86) PCT No.: PCT/US2013/027969
§ 371 (c)(1),
(2) Date: Aug. 26, 2014

(87) PCT Pub. No.: WO2013/130565
PCT Pub. Date: Sep. 6, 2013

(65) Prior Publication Data
US 2015/0064174 A1 Mar. 5, 2015

Related U.S. Application Data

(60) Provisional application No. 61/604,574, filed on Feb. 29, 2012.

(51) Int. Cl.
*C07K 16/08* (2006.01)
*A61K 39/00* (2006.01)
*A61K 39/42* (2006.01)

(52) U.S. Cl.
CPC .............. *C07K 16/085* (2013.01); *A61K 39/42* (2013.01); *A61K 2039/505* (2013.01); *C07K 2316/96* (2013.01); *C07K 2317/24* (2013.01); *C07K 2317/56* (2013.01); *C07K 2317/76* (2013.01)

(58) Field of Classification Search
None
See application file for complete search history.

(56) References Cited

U.S. PATENT DOCUMENTS

2006/0099204 A1* 5/2006 Couto et al. ............... 424/133.1
2010/0115639 A1 5/2010 Goetsch

OTHER PUBLICATIONS

Hague et al., Journal of Infectious Diseases, 2006, 194:584-587.*
Sashihara et al., Virology, 2009, 391:249-256.*
Kunik et al, PLOS Computational Biology, vol. 8, Issue 2, e1002388, pp. 1-12, 2012.
Sashihara et al, Virology, vol. 391, pp. 249-256, 2009.
Hague et al, The Journal of Infectious Diseases, vol. 194, pp. 584-587, 2006.
Hoffman et al, PNAS, 1980, 77: 2979-2983.

* cited by examiner

*Primary Examiner* — Nicole Kinsey White
(74) *Attorney, Agent, or Firm* — Nixon Peabody LLP

(57) ABSTRACT

Described herein are compositions, methods, and uses relating to an EBV-neutralizing antibody.

6 Claims, 9 Drawing Sheets

```
Vh1   1    MGWRWIFLFLLSGTAGVHSEVQLQQSGPELVKPGTSMKISCKASGSSFTDYTMNWMKQSH      60
           M R   +FL+    GV +VQL +SG  LV+PG S K+SC ASG +F+ + M+W++Q+
Vh2   1    MDSRINLVFLVLILKGVQCDVQLVESGGGLVQPGGSRKLSCAASGFTFSSFGMHWVRQAP      60

61   GKNLEWIGLINPYNGGTRYNQKFKGKATLTLDKSSSTAYMEVLSLTSEDSAVYYCAGGLR     120
             K LEW+  I+ +     Y   KG+ T++ D   +T ++++ SL SED+A+YYCA    R
      61   EKGLEWVAYISSGSSTLHYADTVKGRFTISRDNPKNTLFLQMTSLRSEDTAMYYCA---R     117

┌─→ Fc
     112   RVNW----FAYWGQGTLVSVSA│KTTPPSVYPLAPGSAAQTNSMVTLGCLVKGYFPEPVT    176
           N+         YWGQGT V+VS+│KTTPPSVYPLAPGSAAQTNSMVTLGCLVKGYFPEPVT
     118   WGNYPHYAMDYWGQGTSVTVSS│KTTPPSVYPLAPGSAAQTNSMVTLGCLVKGYFPEPVT    177

177   VTWNSGSLSSGVHTFPAVLQSDLYTLSSSVTVPSSTWPSETVTCNVAHPASSTKVDKKIV     236
           VTWNSGSLSSGVHTFPAVLQSDLYTLSSSVTVPSSTWPSETVTCNVAHPASSTKVDKKIV
     178   VTWNSGSLSSGVHTFPAVLQSDLYTLSSSVTVPSSTWPSETVTCNVAHPASSTKVDKKIV     237

237   PRDCGCKPCICTVPEVSSVFIFPPKPKDVLTITLTPKVTCVVVDISKDDPEVQFSWFVDD     296
           PRDCGCKPCICTVPEVSSVFIFPPKPKDVLTITLTPKVTCVVVDISKDDPEVQFSWFVDD
     238   PRDCGCKPCICTVPEVSSVFIFPPKPKDVLTITLTPKVTCVVVDISKDDPEVQFSWFVDD     297

297   VEVHTAQTQPREEQFNSTFRSVSELPIMHQDWLNGKEFKCRVNSAAFPAPIEKTISKTKG     356
           VEVHTAQTQPREEQFNSTFRSVSELPIMHQDWLNGKEFKCRVNSAAFPAPIEKTISKTKG
     298   VEVHTAQTQPREEQFNSTFRSVSELPIMHDQWLNGKEFKCRVNSAAFPAPIEKTISKTKG     357

357   RPKAPQVYTIPPPKEQMAKDKVSLTCMITDFFPEDITVEWQWNGQPAENYKNTQPIMDTD     416
           RPKAPQVYTIPPPKEQMAKDKVSLTCMITDFFPEDITVEWQWNGQPAENYKNTQPIMDTD
     358   RPKAPQVYTIPPPKEQMAKDKVSLTCMITDFFPEDITVEWQWNGQPAENYKNTQPIMDTD     417

417   GSYFVYSKLNVQKSNWEAGNTFTCSVLHEGLHNHHTEKSLSHSPGICPWSPLVLQDSDTY     476
           GSYFVYSKLNVQKSNWEAGNTFTCSVLHEGLHNHHTEKSLSHSPGICPWSPLVLQDSDTY
     418   GSYFVYSKLNVQKSNWEAGNTFTCSVLHEGLHNHHTEKSLSHSPGICPWSPLVLQDSDTY     477

477   LHPSLCK      483
           LHPSLCK
     478   LHPSLCK      484
```

*FIG. 1*

```
                  ┌──► V
K  17   GADG|NIVMTQSPKSMSMSVGERVTLTCKASENVVT---YVSWYQQKPEQSPKLLIYGASN    73
            GA   V+TQ   +++ S GE VTLTC++S    VT   Y +W Q+KP+     LI G +N
L  16   GAIS|QAVLTQE-SALTTSPGETVTLTCRSSTGAVTTSNYANWVQEKPDHLFTGLIGGTNN    74
                                                          ┌──► Fc
   74   RYTGVPDRFTGSGSATDFTLTISSVQAEDLADYHCGQGYSYPYTFGGGTKLEI-|KRADAA   132
        R  GVP RF+GS      LTI+  Q ED A Y C  +S  +  FGGGTKL +|+  ++
   75   RVPGVPARFSGSLIGDKAALTITGAQTEDEAIYFCVLWHSNHWVFGGGTKLTVL|QPKSS   134

133   PTVSIFPPSSEQLTSGGASVVCFLNNFYPKDINVKWKIDGSERQNGVLNSWTDQDSKDST   192
        P+V++FPPSSE+L +   A++VC + +FYP  + V WK+DG+     G+    T Q SK S
  135   PSVTLFPPSSEELETNKATLVCTITDFYPGVVTVDWKVDGTPVTQGMG---TTQPSKQSN   191

193   --YSMSSTLTLTKDEYERHNSYTCEATHKTSTSPIVKSFNRNEC    234
            Y  SS LTLT  +ERH+SY+C+ TH+  T  + KS +R +C
  192   NKYMASSYLTLTARAWERHSSYSCQVTHEGHT-VEKSLSRADC     233
```

*FIG. 3*

L1 Kappa

Signal  FR1  CDR1  FR2  CDR2  FR3
MESQTLVFISILLWLYGADGNIVMTQSPKSMSMSVGERVTLTCKASENVVTYVSWYQQKPEQSPKLLIYGASNRYTGVPDRFTGSG
SATDFTLTISSVQAEDLADYHCGQGYSYPYTFGGGTKLEIK (SEQ ID NO:19)
CDR3  FR4

L2 lambda

Signal  FR1  CDR1  FR2  CDR2  FR3
MAWISLILSLLALSSGAISQAVLTQESALTTSPGETVTLTCRSSTGAVTTSNYANWVQEKPDHLFTGLIGGTNNRVPGVPARFSGSLI
GDKAALTITGAQTEDEAIYFCVLWHSNHWVFGGGTKLTVL (SEQ ID NO:20)
CDR3  FR4

*FIG. 4*

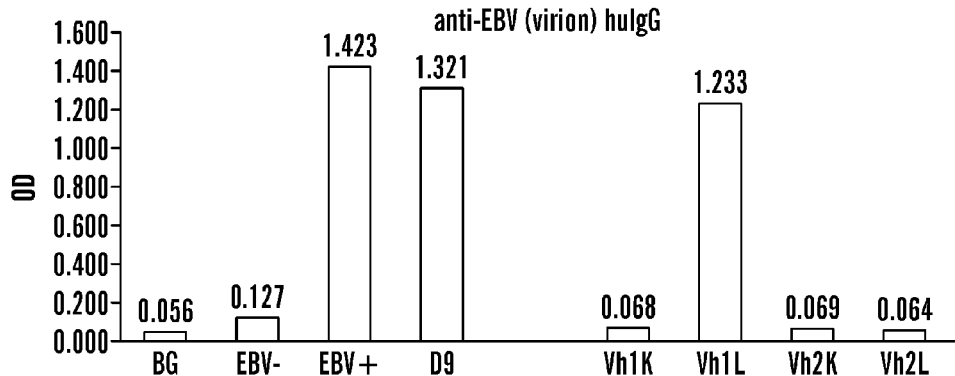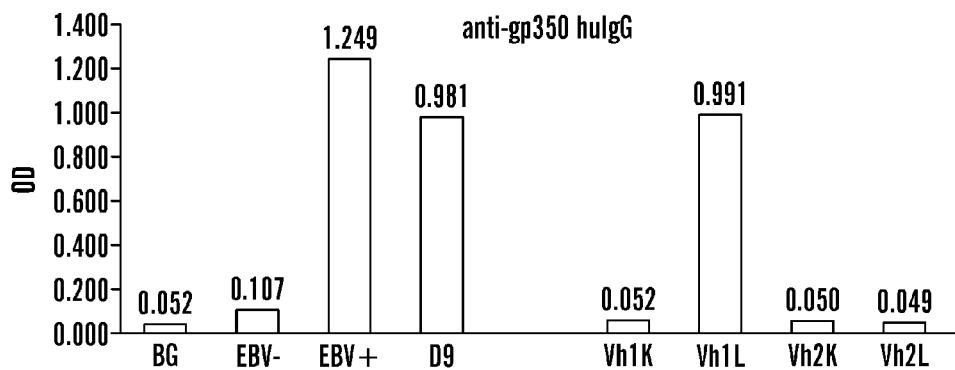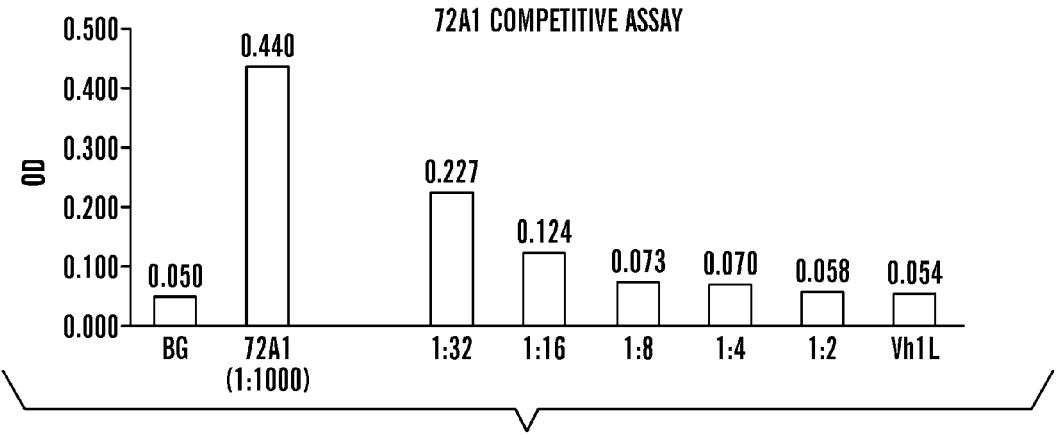
FIG. 9

SEQUENCE LISTING

<160> NUMBER OF SEQ ID NOS: 53

<210> SEQ ID NO 1
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Val Gln Leu Gln Gln Ser Gly Pro Glu Leu Val Lys Pro Gly Thr
1               5                   10                  15

Ser Met Lys Ile Ser Cys Lys Ala Ser Gly Ser Ser Phe Thr Asp Tyr
            20                  25                  30

Thr Met Asn Trp Met Lys Gln Ser His Gly Lys Asn Leu Glu Trp Ile
        35                  40                  45

Gly Leu Ile Asn Pro Tyr Asn Gly Gly Thr Arg Tyr Asn Gln Lys Phe
    50                  55                  60

Lys Gly Lys Ala Thr Leu Thr Leu Asp Lys Ser Ser Ser Thr Ala Tyr
65                  70                  75                  80

Met Glu Val Leu Ser Leu Thr Ser Glu Asp Ser Ala Val Tyr Tyr Cys
                85                  90                  95

Ala Gly Gly Leu Arg Arg Val Asn Trp Phe Ala Tyr Trp Gly Gln Gly
            100                 105                 110

Thr Leu Val Ser Val Ser Ala
        115

<210> SEQ ID NO 2
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Val Gln Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Ser Phe
            20                  25                  30

Gly Met His Trp Val Arg Gln Ala Pro Glu Lys Gly Leu Glu Trp Val
        35                  40                  45

Ala Tyr Ile Ser Ser Gly Ser Ser Thr Leu His Tyr Ala Asp Thr Val
    50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Trp Gly Asn Tyr Pro His Tyr Ala Met Asp Tyr Trp Gly Gln
            100                 105                 110

Gly Thr Ser Val Thr Val Ser Ser
        115                 120

<210> SEQ ID NO 3
<211> LENGTH: 106
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 3

```
Asn Ile Val Met Thr Gln Ser Pro Lys Ser Met Ser Met Ser Val Gly
1               5                   10                  15

Glu Arg Val Thr Leu Thr Cys Lys Ala Ser Glu Asn Val Val Thr Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Thr Gly
50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Gly Tyr Ser Tyr Pro Tyr
                85                  90                  95

Thr Phe Gly Gly Gly Thr Lys Leu Glu Ile
            100                 105
```

<210> SEQ ID NO 4
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

```
Gln Ala Val Leu Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Asn Arg Val Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Val Leu Trp His Ser Asn
                85                  90                  95

His Trp Val Phe Gly Gly Gly Thr Lys Leu Thr Val Leu
            100                 105
```

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

```
Gly Ser Ser Phe Thr Asp Tyr Thr
1               5
```

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ile Asn Pro Tyr Asn Gly Gly Thr
1               5

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ala Gly Gly Leu Arg Arg Val Asn Trp Phe Ala Tyr
1               5                   10

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Phe Thr Phe Ser Ser Phe Gly
1               5

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ile Ser Ser Gly Ser Ser Thr Leu
1               5

<210> SEQ ID NO 10
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ala Arg Trp Gly Asn Tyr Pro His Tyr Ala Met Asp Tyr
1               5                   10

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Glu Asn Val Val Thr Tyr
1               5

<210> SEQ ID NO 12
<211> LENGTH: 3

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Ala Ser
1

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Gln Gly Tyr Ser Tyr Pro Tyr Thr
1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Thr Gly Ala Val Thr Thr Ser Asn Tyr
1               5

<210> SEQ ID NO 15
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Thr Asn
1

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Val Leu Trp His Ser Asn His Trp Val
1               5

<210> SEQ ID NO 17
<211> LENGTH: 138
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 17

Met Gly Trp Arg Trp Ile Phe Leu Phe Leu Leu Ser Gly Thr Ala Gly
1               5                   10                  15

Val His Ser Glu Val Gln Leu Gln Gln Ser Gly Pro Glu Leu Val Lys
            20                  25                  30

Pro Gly Thr Ser Met Lys Ile Ser Cys Lys Ala Ser Gly Ser Ser Phe
        35                  40                  45

Thr Asp Tyr Thr Met Asn Trp Met Lys Gln Ser His Gly Lys Asn Leu
    50                  55                  60

Glu Trp Ile Gly Leu Ile Asn Pro Tyr Asn Gly Gly Thr Arg Tyr Asn
65                  70                  75                  80

Gln Lys Phe Lys Gly Lys Ala Thr Leu Thr Leu Asp Lys Ser Ser Ser
                85                  90                  95

Thr Ala Tyr Met Glu Val Leu Ser Leu Thr Ser Glu Asp Ser Ala Val
            100                 105                 110

Tyr Tyr Cys Ala Gly Gly Leu Arg Arg Val Asn Trp Phe Ala Tyr Trp
        115                 120                 125

Gly Gln Gly Thr Leu Val Ser Val Ser Ala
    130                 135

<210> SEQ ID NO 18
<211> LENGTH: 139
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Met Asp Ser Arg Leu Asn Leu Val Phe Leu Val Leu Ile Leu Lys Gly
1               5                   10                  15

Val Gln Cys Asp Val Gln Leu Val Glu Ser Gly Gly Gly Leu Val Gln
            20                  25                  30

Pro Gly Gly Ser Arg Lys Leu Ser Cys Ala Ala Ser Gly Phe Thr Phe
        35                  40                  45

Ser Ser Phe Gly Met His Trp Val Arg Gln Ala Pro Glu Lys Gly Leu
    50                  55                  60

Glu Trp Val Ala Tyr Ile Ser Ser Gly Ser Ser Thr Leu His Tyr Ala
65                  70                  75                  80

Asp Thr Val Lys Gly Arg Phe Thr Ile Ser Arg Asp Asn Pro Lys Asn
                85                  90                  95

Thr Leu Phe Leu Gln Met Thr Ser Leu Arg Ser Glu Asp Thr Ala Met
            100                 105                 110

Tyr Tyr Cys Ala Arg Trp Gly Asn Tyr Pro His Tyr Ala Met Asp Tyr
        115                 120                 125

Trp Gly Gln Gly Thr Ser Val Thr Val Ser Ser
    130                 135

<210> SEQ ID NO 19
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Met Glu Ser Gln Thr Leu Val Phe Ile Ser Ile Leu Leu Trp Leu Tyr
1               5                   10                  15

Gly Ala Asp Gly Asn Ile Val Met Thr Gln Ser Pro Lys Ser Met Ser
            20                  25                  30

Met Ser Val Gly Glu Arg Val Thr Leu Thr Cys Lys Ala Ser Glu Asn
        35                  40                  45

Val Val Thr Tyr Val Ser Trp Tyr Gln Gln Lys Pro Glu Gln Ser Pro
    50                  55                  60

Lys Leu Leu Ile Tyr Gly Ala Ser Asn Arg Tyr Thr Gly Val Pro Asp
65                  70                  75                  80

Arg Phe Thr Gly Ser Gly Ser Ala Thr Asp Phe Thr Leu Thr Ile Ser
                85                  90                  95

Ser Val Gln Ala Glu Asp Leu Ala Asp Tyr His Cys Gly Gln Gly Tyr
            100                 105                 110

Ser Tyr Pro Tyr Thr Phe Gly Gly Gly Thr Lys Leu Glu Ile Lys
        115                 120                 125

<210> SEQ ID NO 20
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Met Ala Trp Ile Ser Leu Ile Leu Ser Leu Leu Ala Leu Ser Ser Gly
1               5                   10                  15

Ala Ile Ser Gln Ala Val Leu Thr Gln Glu Ser Ala Leu Thr Thr Ser
            20                  25                  30

Pro Gly Glu Thr Val Thr Leu Thr Cys Arg Ser Ser Thr Gly Ala Val
        35                  40                  45

Thr Thr Ser Asn Tyr Ala Asn Trp Val Gln Glu Lys Pro Asp His Leu
    50                  55                  60

Phe Thr Gly Leu Ile Gly Gly Thr Asn Asn Arg Val Pro Gly Val Pro
65                  70                  75                  80

Ala Arg Phe Ser Gly Ser Leu Ile Gly Asp Lys Ala Ala Leu Thr Ile
                85                  90                  95

Thr Gly Ala Gln Thr Glu Asp Glu Ala Ile Tyr Phe Cys Val Leu Trp
            100                 105                 110

His Ser Asn His Trp Val Phe Gly Gly Gly Thr Lys Leu Thr Val Leu
        115                 120                 125

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ctcattcctg ttgaagctgt tgac                                          24

<210> SEQ ID NO 22
<211> LENGTH: 21
<212> TYPE: DNA

-continued

<213> ORGANISM: Artificial Sequence
<220> FEATURE:
<223> OTHER INFORMATION: Description of Artificial Sequence: Synthetic
      primer

<400> SEQUENCE: 22
tatgcaaggc ttacaaccac a                                            21

<210> SEQ ID NO 23
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
acactctgca ggagacagac tcttttc                                      27

<210> SEQ ID NO 24
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
acactcagca cgggacaaac tcttctc                                      27

<210> SEQ ID NO 25
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
caattttctt gtccaccttg gtgctgc                                      27

<210> SEQ ID NO 26
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ctcattcctg ttgaagctct tgacaatggg                                   30

<210> SEQ ID NO 27
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
acactcagca cgggacaaac tcttctccac agt                               33

<210> SEQ ID NO 28
<211> LENGTH: 33
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 28
acactctgca ggagacagac tcttttccac agt                                    33

<210> SEQ ID NO 29
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
acactcagca cgggacaaac tcttctccac agt                                    33

<210> SEQ ID NO 30
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gactcgagtc gacatcgatt tttttttttt ttttt                                  35

<210> SEQ ID NO 31
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
cactgactcg aattcatggg atggaggtgg                                        30

<210> SEQ ID NO 32
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
cacagaccag aattcatgga ctccaggctc                                        30

<210> SEQ ID NO 33
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ggtgtcgtcg tacgtgcaga gacagagacc                                        30

<210> SEQ ID NO 34
<211> LENGTH: 29
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 34
ggtgtcgtcg tacgtgagga gacggtgac                                    29

<210> SEQ ID NO 35
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
cctggtttgt gaattcatgg cctggatttc ac                                32

<210> SEQ ID NO 36
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gacttgggcg tacgtaggac agtcagtttg g                                 31

<210> SEQ ID NO 37
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ccagcatgga attcaagatg gaatcacaga c                                 31

<210> SEQ ID NO 38
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ggtgcagcat ccgtacgttt tatttccagc                                   30

<210> SEQ ID NO 39
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
ggcaaggagt acaagtgc                                                18

<210> SEQ ID NO 40
<211> LENGTH: 18
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 40
gcacggtcac cacgctgc                                                       18

<210> SEQ ID NO 41
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
ggtgtacacc tgtggttc                                                       18

<210> SEQ ID NO 42
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
cgaactgtgg ctgcacc                                                        17

<210> SEQ ID NO 43
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
cctgatgggt gacttcg                                                        17

<210> SEQ ID NO 44
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: a, t, c, or g
<220> FEATURE:
<221> NAME/KEY: modified_base
<222> LOCATION: (6)..(6)
<223> OTHER INFORMATION: a, t, c, or g
<220> FEATURE:
<221> NAME/KEY: modified_base
<222> LOCATION: (9)..(9)
<223> OTHER INFORMATION: a, t, c, or g
<220> FEATURE:
<221> NAME/KEY: modified_base
<222> LOCATION: (15)..(15)
<223> OTHER INFORMATION: a, t, c, or g
<220> FEATURE:
<221> NAME/KEY: modified_base
<222> LOCATION: (24)..(24)
<223> OTHER INFORMATION: a, t, c, or g

<400> SEQUENCE: 44
ggnwsnwsnt tyacngayta yacn                                                24
```

```
<210> SEQ ID NO 45
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)..(9)
<223> OTHER INFORMATION: a, t, c, or g
<220> FEATURE:
<221> NAME/KEY: modified_base
<222> LOCATION: (18)..(18)
<223> OTHER INFORMATION: a, t, c, or g
<220> FEATURE:
<221> NAME/KEY: modified_base
<222> LOCATION: (21)..(21)
<223> OTHER INFORMATION: a, t, c, or g
<220> FEATURE:
<221> NAME/KEY: modified_base
<222> LOCATION: (24)..(24)
<223> OTHER INFORMATION: a, t, c, or g

<400> SEQUENCE: 45
athaayccnt ayaayggngg nacn                                          24

<210> SEQ ID NO 46
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: a, t, c, or g
<220> FEATURE:
<221> NAME/KEY: modified_base
<222> LOCATION: (6)..(6)
<223> OTHER INFORMATION: a, t, c, or g
<220> FEATURE:
<221> NAME/KEY: modified_base
<222> LOCATION: (9)..(9)
<223> OTHER INFORMATION: a, t, c, or g
<220> FEATURE:
<221> NAME/KEY: modified_base
<222> LOCATION: (12)..(12)
<223> OTHER INFORMATION: a, t, c, or g
<220> FEATURE:
<221> NAME/KEY: modified_base
<222> LOCATION: (15)..(15)
<223> OTHER INFORMATION: a, t, c, or g
<220> FEATURE:
<221> NAME/KEY: modified_base
<222> LOCATION: (18)..(18)
<223> OTHER INFORMATION: a, t, c, or g
<220> FEATURE:
<221> NAME/KEY: modified_base
<222> LOCATION: (21)..(21)
<223> OTHER INFORMATION: a, t, c, or g
<220> FEATURE:
<221> NAME/KEY: modified_base
<222> LOCATION: (33)..(33)
<223> OTHER INFORMATION: a, t, c, or g

<400> SEQUENCE: 46
gcnggnggny tnmgnmgngt naaytggtty gcntay                             36

<210> SEQ ID NO 47
<211> LENGTH: 27
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: a, t, c, or g
<220> FEATURE:
<221> NAME/KEY: modified_base
<222> LOCATION: (6)..(6)
<223> OTHER INFORMATION: a, t, c, or g
<220> FEATURE:
<221> NAME/KEY: modified_base
<222> LOCATION: (9)..(9)
<223> OTHER INFORMATION: a, t, c, or g
<220> FEATURE:
<221> NAME/KEY: modified_base
<222> LOCATION: (12)..(12)
<223> OTHER INFORMATION: a, t, c, or g
<220> FEATURE:
<221> NAME/KEY: modified_base
<222> LOCATION: (15)..(15)
<223> OTHER INFORMATION: a, t, c, or g
<220> FEATURE:
<221> NAME/KEY: modified_base
<222> LOCATION: (18)..(18)
<223> OTHER INFORMATION: a, t, c, or g
<220> FEATURE:
<221> NAME/KEY: modified_base
<222> LOCATION: (21)..(21)
<223> OTHER INFORMATION: a, t, c, or g

<400> SEQUENCE: 47
acnggngcng tnacnacnws naaytay                                          27

<210> SEQ ID NO 48
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: a, t, c, or g
<220> FEATURE:
<221> NAME/KEY: modified_base
<222> LOCATION: (6)..(6)
<223> OTHER INFORMATION: a, t, c, or g

<400> SEQUENCE: 48 ggnacnaay                                                               9

<210> SEQ ID NO 49
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: a, t, c, or g
<220> FEATURE:
<221> NAME/KEY: modified_base
<222> LOCATION: (6)..(6)
<223> OTHER INFORMATION: a, t, c, or g
<220> FEATURE:
<221> NAME/KEY: modified_base
<222> LOCATION: (15)..(15)
<223> OTHER INFORMATION: a, t, c, or g
<220> FEATURE:
<221> NAME/KEY: modified_base
```

<222> LOCATION: (27)..(27)
<223> OTHER INFORMATION: a, t, c, or g

<400> SEQUENCE: 49
gtnytntggc aywsnaayca ytgggtn                                          27

<210> SEQ ID NO 50
<211> LENGTH: 483
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Met Gly Trp Arg Trp Ile Phe Leu Phe Leu Leu Ser Gly Thr Ala Gly
1               5                   10                  15

Val His Ser Glu Val Gln Leu Gln Gln Ser Gly Pro Glu Leu Val Lys
            20                  25                  30

Pro Gly Thr Ser Met Lys Ile Ser Cys Lys Ala Ser Gly Ser Ser Phe
        35                  40                  45

Thr Asp Tyr Thr Met Asn Trp Met Lys Gln Ser His Gly Lys Asn Leu
    50                  55                  60

Glu Trp Ile Gly Leu Ile Asn Pro Tyr Asn Gly Gly Thr Arg Tyr Asn
65                  70                  75                  80

Gln Lys Phe Lys Gly Lys Ala Thr Leu Thr Leu Asp Lys Ser Ser Ser
                85                  90                  95

Thr Ala Tyr Met Glu Val Leu Ser Leu Thr Ser Glu Asp Ser Ala Val
            100                 105                 110

Tyr Tyr Cys Ala Gly Gly Leu Arg Arg Val Asn Trp Phe Ala Tyr Trp
        115                 120                 125

Gly Gln Gly Thr Leu Val Ser Val Ser Ala Ala Lys Thr Thr Pro Pro
    130                 135                 140

Ser Val Tyr Pro Leu Ala Pro Gly Ser Ala Ala Gln Thr Asn Ser Met
145                 150                 155                 160

Val Thr Leu Gly Cys Leu Val Lys Gly Tyr Phe Pro Glu Pro Val Thr
                165                 170                 175

Val Thr Trp Asn Ser Gly Ser Leu Ser Ser Gly Val His Thr Phe Pro
            180                 185                 190

Ala Val Leu Gln Ser Asp Leu Tyr Thr Leu Ser Ser Ser Val Thr Val
        195                 200                 205

Pro Ser Ser Thr Trp Pro Ser Glu Thr Val Thr Cys Asn Val Ala His
    210                 215                 220

Pro Ala Ser Ser Thr Lys Val Asp Lys Lys Ile Val Pro Arg Asp Cys
225                 230                 235                 240

Gly Cys Lys Pro Cys Ile Cys Thr Val Pro Glu Val Ser Ser Val Phe
                245                 250                 255

Ile Phe Pro Pro Lys Pro Lys Asp Val Leu Thr Ile Thr Leu Thr Pro
            260                 265                 270

Lys Val Thr Cys Val Val Asp Ile Ser Lys Asp Asp Pro Glu Val
        275                 280                 285

Gln Phe Ser Trp Phe Val Asp Asp Val Glu Val His Thr Ala Gln Thr
    290                 295                 300

Gln Pro Arg Glu Glu Gln Phe Asn Ser Thr Phe Arg Ser Val Ser Glu
305                 310                 315                 320

```
Leu Pro Ile Met His Gln Asp Trp Leu Asn Gly Lys Glu Phe Lys Cys
                325                 330                 335

Arg Val Asn Ser Ala Ala Phe Pro Ala Pro Ile Glu Lys Thr Ile Ser
            340                 345                 350

Lys Thr Lys Gly Arg Pro Lys Ala Pro Gln Val Tyr Thr Ile Pro Pro
        355                 360                 365

Pro Lys Glu Gln Met Ala Lys Asp Lys Val Ser Leu Thr Cys Met Ile
    370                 375                 380

Thr Asp Phe Phe Pro Glu Asp Ile Thr Val Glu Trp Gln Trp Asn Gly
385                 390                 395                 400

Gln Pro Ala Glu Asn Tyr Lys Asn Thr Gln Pro Ile Met Asp Thr Asp
                405                 410                 415

Gly Ser Tyr Phe Val Tyr Ser Lys Leu Asn Val Gln Lys Ser Asn Trp
            420                 425                 430

Glu Ala Gly Asn Thr Phe Thr Cys Ser Val Leu His Glu Gly Leu His
        435                 440                 445

Asn His His Thr Glu Lys Ser Leu Ser His Ser Pro Gly Ile Cys Pro
    450                 455                 460

Trp Ser Pro Leu Val Leu Gln Asp Ser Asp Thr Tyr Leu His Pro Ser
465                 470                 475                 480

Leu Cys Lys

<210> SEQ ID NO 51
<211> LENGTH: 484
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Met Asp Ser Arg Leu Asn Leu Val Phe Leu Val Leu Ile Leu Lys Gly
1               5                   10                  15

Val Gln Cys Asp Val Gln Leu Val Glu Ser Gly Gly Gly Leu Val Gln
            20                  25                  30

Pro Gly Gly Ser Arg Lys Leu Ser Cys Ala Ala Ser Gly Phe Thr Phe
        35                  40                  45

Ser Ser Phe Gly Met His Trp Val Arg Gln Ala Pro Glu Lys Gly Leu
    50                  55                  60

Glu Trp Val Ala Tyr Ile Ser Ser Gly Ser Ser Thr Leu His Tyr Ala
65                  70                  75                  80

Asp Thr Val Lys Gly Arg Phe Thr Ile Ser Arg Asp Asn Pro Lys Asn
                85                  90                  95

Thr Leu Phe Leu Gln Met Thr Ser Leu Arg Ser Glu Asp Thr Ala Met
            100                 105                 110

Tyr Tyr Cys Ala Arg Trp Gly Asn Tyr Pro His Tyr Ala Met Asp Tyr
        115                 120                 125

Trp Gly Gln Gly Thr Ser Val Thr Val Ser Ser Ala Lys Thr Thr Pro
    130                 135                 140

Pro Ser Val Tyr Pro Leu Ala Pro Gly Ser Ala Ala Gln Thr Asn Ser
145                 150                 155                 160

Met Val Thr Leu Gly Cys Leu Val Lys Gly Tyr Phe Pro Glu Pro Val
                165                 170                 175

Thr Val Thr Trp Asn Ser Gly Ser Leu Ser Ser Gly Val His Thr Phe
            180                 185                 190
```

-continued

```
Pro Ala Val Leu Gln Ser Asp Leu Tyr Thr Leu Ser Ser Val Thr
        195                 200                 205

Val Pro Ser Ser Thr Trp Pro Ser Glu Thr Val Thr Cys Asn Val Ala
    210                 215                 220

His Pro Ala Ser Ser Thr Lys Val Asp Lys Lys Ile Val Pro Arg Asp
225                 230                 235                 240

Cys Gly Cys Lys Pro Cys Ile Cys Thr Val Pro Glu Val Ser Ser Val
                245                 250                 255

Phe Ile Phe Pro Pro Lys Pro Lys Asp Val Leu Thr Ile Thr Leu Thr
            260                 265                 270

Pro Lys Val Thr Cys Val Val Val Asp Ile Ser Lys Asp Asp Pro Glu
        275                 280                 285

Val Gln Phe Ser Trp Phe Val Asp Asp Val Glu Val His Thr Ala Gln
    290                 295                 300

Thr Gln Pro Arg Glu Glu Gln Phe Asn Ser Thr Phe Arg Ser Val Ser
305                 310                 315                 320

Glu Leu Pro Ile Met His Gln Asp Trp Leu Asn Gly Lys Glu Phe Lys
                325                 330                 335

Cys Arg Val Asn Ser Ala Ala Phe Pro Ala Pro Ile Glu Lys Thr Ile
            340                 345                 350

Ser Lys Thr Lys Gly Arg Pro Lys Ala Pro Gln Val Tyr Thr Ile Pro
        355                 360                 365

Pro Pro Lys Glu Gln Met Ala Lys Asp Lys Val Ser Leu Thr Cys Met
    370                 375                 380

Ile Thr Asp Phe Phe Pro Glu Asp Ile Thr Val Glu Trp Gln Trp Asn
385                 390                 395                 400

Gly Gln Pro Ala Glu Asn Tyr Lys Asn Thr Gln Pro Ile Met Asp Thr
                405                 410                 415

Asp Gly Ser Tyr Phe Val Tyr Ser Lys Leu Asn Val Gln Lys Ser Asn
            420                 425                 430

Trp Glu Ala Gly Asn Thr Phe Thr Cys Ser Val Leu His Glu Gly Leu
        435                 440                 445

His Asn His His Thr Glu Lys Ser Leu Ser His Ser Pro Gly Ile Cys
    450                 455                 460

Pro Trp Ser Pro Leu Val Leu Gln Asp Ser Asp Thr Tyr Leu His Pro
465                 470                 475                 480

Ser Leu Cys Lys
```

```
<210> SEQ ID NO 52
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Gly Ala Asp Gly Asn Ile Val Met Thr Gln Ser Pro Lys Ser Met Ser
1               5                   10                  15

Met Ser Val Gly Glu Arg Val Thr Leu Thr Cys Lys Ala Ser Glu Asn
            20                  25                  30

Val Val Thr Tyr Val Ser Trp Tyr Gln Gln Lys Pro Glu Gln Ser Pro
        35                  40                  45

Lys Leu Leu Ile Tyr Gly Ala Ser Asn Arg Tyr Thr Gly Val Pro Asp
    50                  55                  60
```

```
Arg Phe Thr Gly Ser Gly Ser Ala Thr Asp Phe Thr Leu Thr Ile Ser
 65                  70                  75                  80

Ser Val Gln Ala Glu Asp Leu Ala Asp Tyr His Cys Gly Gln Gly Tyr
                 85                  90                  95

Ser Tyr Pro Tyr Thr Phe Gly Gly Gly Thr Lys Leu Glu Ile Lys Arg
            100                 105                 110

Ala Asp Ala Ala Pro Thr Val Ser Ile Phe Pro Pro Ser Ser Glu Gln
        115                 120                 125

Leu Thr Ser Gly Gly Ala Ser Val Val Cys Phe Leu Asn Asn Phe Tyr
    130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
        195                 200                 205

Ile Val Lys Ser Phe Asn Arg Asn Glu Cys
    210                 215

<210> SEQ ID NO 53
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Gly Ala Ile Ser Gln Ala Val Leu Thr Gln Glu Ser Ala Leu Thr Thr
  1               5                  10                  15

Ser Pro Gly Glu Thr Val Thr Leu Thr Cys Arg Ser Ser Thr Gly Ala
                 20                  25                  30

Val Thr Thr Ser Asn Tyr Ala Asn Trp Val Gln Glu Lys Pro Asp His
             35                  40                  45

Leu Phe Thr Gly Leu Ile Gly Gly Thr Asn Asn Arg Val Pro Gly Val
     50                  55                  60

Pro Ala Arg Phe Ser Gly Ser Leu Ile Gly Asp Lys Ala Ala Leu Thr
 65                  70                  75                  80

Ile Thr Gly Ala Gln Thr Glu Asp Glu Ala Ile Tyr Phe Cys Val Leu
                 85                  90                  95

Trp His Ser Asn His Trp Val Phe Gly Gly Gly Thr Lys Leu Thr Val
            100                 105                 110

Leu Gly Gln Pro Lys Ser Ser Pro Ser Val Thr Leu Phe Pro Pro Ser
        115                 120                 125

Ser Glu Glu Leu Glu Thr Asn Lys Ala Thr Leu Val Cys Thr Ile Thr
    130                 135                 140

Asp Phe Tyr Pro Gly Val Val Thr Val Asp Trp Lys Val Asp Gly Thr
145                 150                 155                 160

Pro Val Thr Gln Gly Met Gly Thr Thr Gln Pro Ser Lys Gln Ser Asn
                165                 170                 175

Asn Lys Tyr Met Ala Ser Ser Tyr Leu Thr Leu Thr Ala Arg Ala Trp
            180                 185                 190
```

```
Glu Arg His Ser Ser Tyr Ser Cys Gln Val Thr His Glu Gly His Thr
        195                 200                 205

Val Glu Lys Ser Leu Ser Arg Ala Asp Cys
    210                 215
```

NEUTRALIZING ANTIBODY FOR EPSTEIN BARR VIRUS-ASSOCIATED DISEASE

CROSS-REFERENCE TO RELATED APPLICATIONS

This application is a 35 U.S.C. §371 National Phase Entry Application of International Application No. PCT/US2013/027969 filed Feb. 27, 2013, which designates the U.S., and which claims benefit under 35 U.S.C. §119(e) of U.S. Provisional Application No. 61/604,574 filed Feb. 29, 2012, the contents of which are incorporated herein by reference in their entirety.

GOVERNMENT SUPPORT

This invention was made with Government support under Grant No. DE018926 awarded by the National Institutes of Health. The Government has certain rights in the invention.

SEQUENCE LISTING

The instant application contains a Sequence Listing which has been submitted in ASCII format via EFS-Web and is hereby incorporated by reference in its entirety. Said ASCII copy, created on Jan. 3, 2013, is named 43214733.txt and is 33,730 bytes in size.

FIELD

The present invention relates to neutralizing antibodies targeting Epstein Barr virus (EBV), and compositions and methods comprising such antibodies useful in treating or preventing EBV-associated diseases.

BACKGROUND

Epstein-Ban virus (EBV) is a herpesvirus (human herpesvirus 4) that infects nearly all humans by adulthood. Primary EBV infection is the most common cause of Infectious Mononucleosis. Hospitalization of young adults suffering from Infectious Mononucleosis is about 30%, and the annual costs for hospitalization exceed several hundred $million annually. EBV infection is also associated with the development of several malignancies including Burkitt Lymphoma, Hodgkin Lymphoma, nasopharyngeal carcinoma, gastric carcinoma, and B-lymphoproliferative disorders in immunosuppressed patients. Patients who are EBV seronegative and immunosuppressed, e.g., those with genetic immunodeficiencies, AIDS, or those undergoing organ or stem cell transplantation, are at increased (e.g. high) risk for EBV-induced lymphoproliferative disease if they become EBV-infected while immunosuppressed, probably due to the impaired development of EBV-specific immunity and uncontrolled EBV infection of B-cells during primary EBV infection. There remains an urgent need for prophylactic, pre-emptive and treatment strategies for management of EBV-associated disease.

SUMMARY

The present embodiments provide for recombinant, humanized EBV-neutralizing antibodies, compositions comprising recombinant, humanized EBV-neutralizing antibodies, and treatments comprising administration of these antibodies to prevent or ameliorate EBV-associated diseases. More specifically, administration of compositions comprising recombinant, humanized EBV-neutralizing antibodies may slow the viral amplification during primary EBV infection, thereby allowing for a more gentle development of an adaptive immune response to EBV infection and reduced risk for infectious mononucleosis (IM). Furthermore, compositions comprising recombinant, humanized EBV-neutralizing antibodies may slow viral amplification during primary EBV infection and reduce the risk of B-lymphoproliferative disease in immunosuppressed hosts by maintaining a more equal balance between the expansion of EBV-infected B-cells and the weakened immune response. Treatment with, e.g., recombinant, humanized EBV-neutralizing antibodies may provide effective prophylactic treatment for preventing EBV-induced lymphoproliferative disease in immunosuppressed hosts.

An embodiment of the present invention provides for a purified or isolated recombinant anti-EBV antibody comprising partially or fully humanized amino acid residues. In a specific embodiment, the antibody comprises murine variable regions of heavy and light chains, cloned in-frame with the human immunoglobulin constant regions in order to express recombinant humanized forms of murine immunoglobulin light and heavy chain. In a specific embodiment, the recombinant humanized antibody binds EBV antigen gp350. In another specific embodiment, the recombinant humanized antibody neutralizes EBV infection.

In a particular embodiment, the recombinant, humanized EBV-neutralizing antibody has a heavy chain comprising the amino acid residues designated Vh1, as depicted in FIG. 1 (SEQ ID NO:1). In a particular embodiment, the humanized antibody has a heavy chain comprising the amino acid residues designated Vh2, as depicted in FIG. 1 (SEQ ID NO:2). In a particular embodiment, the humanized antibody has a kappa light chain comprising the amino acid residues as depicted in FIG. 3 (SEQ ID NO:3). In a particular embodiment, the humanized antibody has a lambda light chain comprising the amino acid residues as depicted in FIG. 3 (SEQ ID NO:4).

In another particular embodiment, the recombinant humanized EBV-neutralizing antibody comprises a heavy chain comprising the amino acid residues designated Vh1, as depicted in FIG. 1 (SEQ ID NO:1) and a lambda light chain comprising the amino acid residues designated IgL, as depicted in FIG. 3 (SEQ ID NO:4).

In yet another embodiment, the recombinant humanized EBV neutralizing antibody has a heavy chain comprising a CDR H1 with amino acids GSSFTDYT (SEQ ID NO:5), a CDR H2 with amino acids INPYNGGT (SEQ ID NO:6), and a CDR H3 with amino acids AGGLRRVNWFAY (SEQ ID NO:7).

In another embodiment, the recombinant humanized EBV neutralizing antibody has a heavy chain comprising a CDR H1 with amino acids GFTFSSFG (SEQ ID NO:8), a CDR H2 with amino acids ISSGSSTL (SEQ ID NO:9), and a CDR H3 with amino acids ARWGNYPHYAMDY (SEQ ID NO:10).

In another embodiment, the recombinant humanized EBV neutralizing antibody has a light chain comprising a CDR L1 with amino acids ENVVTY (SEQ ID NO:11), a CDR L2 with amino acids GAS (SEQ ID NO:12), and a CDR L3 with amino acids GQGYSYPYT (SEQ ID NO:13).

In yet another embodiment, the recombinant humanized EBV neutralizing antibody has a light chain comprising a CDR L1 with amino acids TGAVTTSNY (SEQ ID NO:14), a CDR L2 with amino acids GTN (SEQ ID NO:15), and a CDR L3 with amino acids VLWHSNHWV (SEQ ID NO:16).

In another embodiment of the invention, the recombinant humanized EBV neutralizing antibody comprises a heavy chain component comprising a CDR H1 with amino acids GSSFTDYT (SEQ ID NO:5), a CDR H2 with amino acids INPYNGGT (SEQ ID NO:6), and a CDR H3 with amino acids AGGLRRVNWFAY (SEQ ID NO:7); and a light chain component comprising a CDR L1 with amino acids TGAVTTSNY (SEQ ID NO:14), a CDR L2 with amino acids GTN (SEQ ID NO:15), and a CDR L3 with amino acids VLWHSNHWV (SEQ ID NO:16).

Another embodiment of the present invention provides for administering to a subject in need, for example, a pediatric patient suffering from genetic immunodeficiency, a therapeutic dose of a recombinant, humanized EBV-neutralizing antibody described herein for the prevention EBV-induced lymphoproliferative disease. In a particular embodiment, the administered antibody comprises a heavy chain component comprising a CDR H1 with amino acids GSSFTDYT (SEQ ID NO:5), a CDR H2 with amino acids INPYNGGT (SEQ ID NO:6), and a CDR H3 with amino acids AGGLRRVNWFAY (SEQ ID NO:7); and a light chain component comprising a CDR L1 with amino acids TGAVTTSNY (SEQ ID NO:14), a CDR L2 with amino acids GTN (SEQ ID NO:15), and a CDR L3 with amino acids VLWHSNHWV (SEQ ID NO:16). In a particular embodiment, the administered antibody comprises a heavy chain comprising the amino acid residues designated Vh1, as depicted in FIG. 1 (SEQ ID NO:1) and a lambda light chain comprising the amino acid residues designated IgL, as depicted in FIG. 3 (SEQ ID NO:4). In another embodiment, the pediatric immunodeficiency is X-linked lymphoproliferative disease.

In some embodiments of any of the aspects described herein, the subject in need can be a subject who is immunosuppressed. In some embodiments, the immunosuppressed subject can be one who has been administered immunosuppressive drugs, e.g. after transplantation. In some embodiments, the immunosuppressed subject can be a subject who has received radiation treatment. In some embodiments, the immunosuppressed subject can be a subject who has or has been diagnosed with AIDS. In some embodiments, the immunosuppressed subject can be a subject who has or has been diagnosed with a genetic immunodeficiency.

DESCRIPTION OF THE DRAWINGS

FIG. 1 presents the amino acids of two immunoglobulin heavy chains cloned from the 72A1 hybridoma cell line (SEQ ID NOS 50 and 51, respectively, in order of appearance). The variable chain region of the antibody heavy chains start at amino acid 20 of the presented amino acid sequence, and continues to the Fc chain (arrow).

FIG. 3 presents the amino acids of two immunoglobulin light chains, one lambda and one kappa, cloned from the 72A1 hybridoma cell line (SEQ ID NOS 52 and 53, respectively, in order of appearance). The variable chain regions are indicated by the arrows.

FIG. 4 is a scheme showing signal peptide, CDRs, and FRs within the variable regions of the kappa and lambda chains of FIG. 3.

FIG. 9 is a series of bar graphs showing data from immunoassays in which Vh1L derived from recombinant host cell supernatants bound to EBV virions, bound to EBV gp350, and competes with supernatants from 721A1 cell line for gp350 binding.

DETAILED DESCRIPTION

Figure 2:
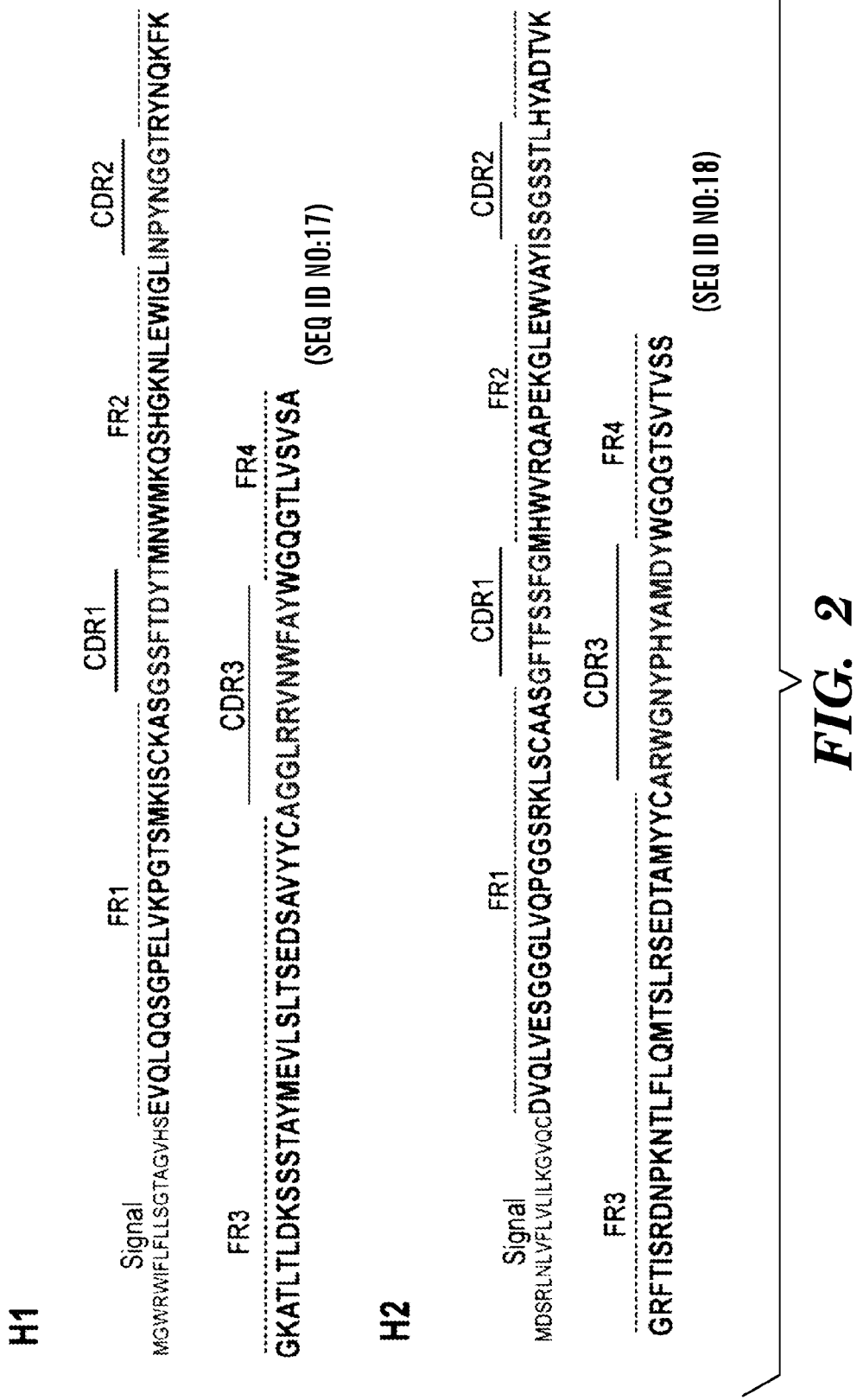
FIG. 2 is a scheme showing the signal peptide, FRs, and CDRs within the variable regions of Vh1 and Vh2.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. The term "or" is inclusive unless modified, for example, by "either." Other than in the operating examples, or where otherwise indicated, all numbers expressing quantities of ingredients or reaction conditions used herein should be understood as modified in all instances by the term "about."

Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

The present embodiments relate to EBV-neutralizing antibodies, compositions comprising EBV-neutralizing antibodies, and treatments comprising administration of these to prevent or ameliorate EBV-associated diseases.

EBV was identified in 1964 as a lymphotropic herpes virus of man. EBV is ubiquitous in all human populations and is spread by horizontal transmission. In economically emerging countries, 99.9% of children are infected by about 3 years of age. Interestingly, when infection is delayed until adolescence or beyond, more typically the case in economically developed countries, primary infection with acute mononucleosis occurs in about 50% of those infected. IM typically presents with an acute onset of malaise, fever, sore throat, splenomegaly, and enlarged lymph nodes. In healthy hosts, the disease is usually self-limiting, and runs its course with development of effective cellular and humoral immunological responses. However, the immune responses do not fully clear EBV infection, and EBV infection persists for life asymptomatically and at low levels in most individuals. Occasionally, the persistent EBV infection can lead to development of EBV-positive malignancies including Burkitt Lymphoma, Hodgkin Lymphoma, nasopharyngeal carcinoma, and gastric carcinoma The crucial and delicate nature of the specific humoral and cellular responses to EBV virus infection become evident at their failure. EBV-infected hosts who become immunosuppressed, for example, by HIV infection or by administration of immunosuppressive drugs post organ transplantation or for autoimmune diseases, are at risk for B-lymphoproliferative disorders and B cell lymphomas. Patients who are EBV seronegative and immunosuppressed, e.g., children with genetic immunodeficiencies, AIDS, or those undergoing organ or stem cell transplantation, are at even greater risk for EBV-induced lymphoproliferative disease, as well as fatal IM, aplastic anemias, and B cell lymphomas. Hence, the development of an EBV vaccine has been urged for decades. See, e.g., Epstein et al., 53 Clin. Exp. Immunol. 257 (1983). Yet, to date there is no commercially available vaccine.

A particular EBV-associated disease for which the present invention provides a novel treatment is X-linked lymphoproliferative disease (XLP). XLP is a primary immunodeficiency caused by mutations in the SH2D1A gene, which encodes a cytoplasmic component, SAP. SAP functions in signaling pathways in certain populations of immune cells. A defining feature of XLP is exquisite sensitivity to infection with EBV (but not other microbial pathogens). Because EBV selectively infects B-cells, the exquisite sensitivity in XLP to EBV infection results from the ability of the virus to sequester itself in B-cells, which can only induce a cytotoxic T-cell response in SAP-sufficient cells. Thus, the functional defect in SAP-deficient CD8+ T cells does not relate to EBV itself, but rather to the nature of the target cell presenting viral epitopes. Although EBV infection in normal individuals is generally innocuous, in XLP it can be fatal. See Palendira et al., 9 PLoS Biol. e1001187 (2011).

Cell surface-associated viral glycoproteins are thought to play a major role as target antigens in cellular cytotoxicity and antiviral immunosurveillance. One such glycoprotein is the Epstein-Barr virus (EBV)-encoded glycoprotein 350 (gp350), which is expressed on both virion envelopes and EBV producer cells and carries the virus attachment protein moiety. Some antibodies to gp350 can neutralize the virus, and gp350 is a target antigen for EBV-specific antibody-dependent cellular cytotoxicity (ADCC). Khyatti et al., Epstein-Barr virus (EBV) glycoprotein gp350 expressed on transfected cells resistant to natural killer cell activity serves as a target antigen for EBV-specific antibody-dependent cellular cytotoxicity, 65 J. Virol. 996 (1991).

A recent phase II clinical trial showed that a subunit vaccine consisting of the EBV membrane glycoprotein, gp350, can reduce the incidence of EBV-associated infectious mononucleosis (IM). Sokal et al., 196 J. Infect. Dis. 1749 (2007). Neither the mechanism by which primary EBV infection causes IM, nor how the gp350 vaccine might prevent IM, are known. The gp350 vaccine can induce EBV-neutralizing antibodies, but it is not known how EBV-neutralizing antibodies affect primary EBV infection, nor whether neutralizing antibodies are important for vaccine efficacy. Indeed, the vaccine had no efficacy in preventing asymptomatic EBV infection. Moreover, although the gp350 vaccine can effectively induce neutralizing antibodies in healthy patients, it is a less effective immunogen in immunosuppressed hosts.

Given the uncertainty regarding the efficacy of traditional vaccine approaches to preventing of ameliorating EBV-associated diseases, the present invention provides for a new approach that utilizes passive immunity. More specifically, administration of compositions comprising purified, recombinant, humanized EBV-neutralizing antibodies can slow the viral amplification during primary EBV infection, thereby allowing for a more robust development of an adaptive immune response to EBV infection, and reduced risk for IM. The EBV-neutralizing antibodies of the present invention can slow viral amplification during primary EBV infection and reduce the risk of B-lymphoproliferative disease in immunosuppressed hosts by maintaining a more equal balance between the expansion of EBV-infected B-cells and the weakened immune response. EBV-neutralizng antibodies (e.g. adoptive transfer of EBV-neutralizing antibodies) can provide effective prophylactic treatment for preventing EBV-induced lymphoproliferative disease in immunosuppressed hosts.

As used herein, "immunosuppressed" refers to a subject with an innate, acquired, or induced inability (e.g. a reduced ability) to develop a normal immune response. Immunocompromised individuals thus include those with primary (e.g. hereditary) and acquired immunodeficiencies. Immunocompromised subjects include, without limitation, subjects suffering from most forms of cancer, subjects which have received chemotherapy or other immunosuppressing treatment, such as induced by treatment with steroids, cyclophosphamide, azathioprine, methotrexate, cyclosporine or rapamycin, in particular in relation to cancer treatment or the treatment or prevention of transplant rejection, subjects suffering from different diseases such as AIDS or leukemia, an immunodeficiency due to some pathogenic infections or malnutrition, subjects suffering sickle cell anemia, subjects suffering cystic fibrosis, subjects who do not have a spleen, subjects with end stage kidney disease (dialysis), subjects who have been under treatment with corticosteroids, subjects who have received ionizing radiation of various types and strength (e.g. photon, electron, helium nucleus).

An embodiment of the present invention provides for a recombinant, humanized monoclonal antibody that binds to EBV gp350. "Antibody", in the context of the present invention, refers to a wide variety of EBV-neutralizing antigen-binding peptides that can be assembled into any structure, proteinaceous or otherwise, to bind to and neutralize EBV. For example, the anti-EBV gp350, EBV-neutralizing antibody of the present invention includes, but is not limited to, synthetic antibodies, monoclonal antibodies, recombinantly produced antibodies, multispecific antibodies (including bi-specific antibodies), human antibodies, humanized antibodies, CDR-grafted antibodies, resurfaced humanized antibodies, chimeric antibodies, intrabodies, single-chain Fvs (scFv) (e.g., including monospecific, bispecific, etc.), Fab fragments, F(ab') fragments, disulfide-linked Fvs (sdFv), anti-idiotypic (anti-Id) antibodies, and epitope-binding portions or fragments of any of these.

In particular, antibodies of the present invention include immunoglobulin molecules and immunologically active portions of immunoglobulin molecules, i.e., molecules that contain an antigen-binding site that immunospecifically binds to an EBV-neutralizing antigen (e.g., one or more complementarity determining regions (CDRs) of an anti-EBV-antigen antibody). The antibodies of the invention can be of any type (e.g., IgG, IgE, IgM, IgD, IgA and IgY), any class (e.g., IgG1, IgG2, IgG3, IgG4, IgA1 and IgA2), or any subclass (e.g., IgG2a and IgG2b) of immunoglobulin molecule. For example, modified antibodies can be IgG antibodies, or a class (e.g., human IgG1) or subclass thereof. In sum, as used herein, "antibody" refers to any peptide having a neutralizing EBV-antigen-binding region. Accordingly, the type of antibody or portion thereof can be selected for use according to the present invention based on the desired characteristics and functions that are desired for a particular therapeutic or diagnostic use, such as but not limited to serum half-life, intravascular distribution, complement fixation, etc.

As used herein, the term "antigen-binding region" refers to that portion of an antibody molecule which contains the amino acid residues that interact with an antigen and confer on the antibody its specificity and affinity for the antigen. The antibody region typically includes the "framework" amino acid residues necessary to maintain the proper conformation of the antigen-binding residues.

For example, antigen-binding region of antibodies includes the "complementarity determining regions" or "CDR" regions. These CDR regions account for the basic specificity of the antibody for a particular antigenic determinant structure. The CDRs represent non-contiguous stretches of amino acids within the variable regions but, regardless of species, the positional locations of these critical amino acid sequences within the variable heavy and light chain regions have been found to have similar locations within the amino acid sequences of the variable chains. The variable heavy and light chains of all antibodies each have three CDR regions, each non-contiguous with the others (termed L1, L2, L3, H1, H2, H3) for the respective light (L) and heavy (H) chains. The accepted CDR regions have been described by Kabat et al., 252 J. Biol. Chem. 6609 (1977), and CDR loops may be identified by applying these rules during an examination of a linear amino acid sequence. The rules for defining the CDR-H3 loop can vary, however (see Chapter 4, Antibody Engin. Met. & Protocols (Lo, ed. Humana Press, Totowa, N.J., 2004)), and the actual boundaries of some CDR-H3 loops may not be identified without experimental techniques such as circular dichroism, nuclear magnetic resonance, or X-ray crystallography. Nevertheless, the predicted CDRs of the present recombinant, humanized antibodies are indicated in FIGS. 2 and 4.

Regarding the antigenic determinate recognized by the CDR regions of the antibody, this is also referred to as the "epitope." In other words, epitope refers to that portion of any molecule capable of being recognized by, and bound by, an antibody (the corresponding antibody binding region may be referred to as a paratope). In general, epitopes consist of chemically active surface groupings of molecules, for example, amino acids or sugar side chains, and have specific three-dimensional structural characteristics as well as specific charge characteristics.

An "antigen" is a molecule or a portion of a molecule capable of being bound by an antibody which is additionally capable of inducing an animal to produce an antibody capable of binding to an epitope of that antigen. An antigen may have one or more than one epitope. The specific reaction referred to above is meant to indicate that the antigen will react, in a highly selective manner, with its corresponding antibody and not with the multitude of other antibodies which may be evoked by other antigens.

The EBV-neutralizing antibody of the present invention can optionally further at least one of: bind EBV gp350 epitope with an affinity of at least one selected from at least $10^{-9}$ M, at least $10^{-10}$ M, at least $10^{-11}$ M, or at least $10^{-12}$ M; substantially neutralizes EBV. Methods for determining monoclonal antibody specificity and affinity by competitive inhibition are known by those of ordinary skill in the art. See, e.g., Antibodies: A Lab. Manual (Harlow et al., eds., Cold Spring Harbor Lab. Press, Cold Spring Harbor, N.Y., 1988); Current Protocols in Immunol. (Colligan et al., eds., Greene Pub. Assoc. & Wiley Interscience, NY, 1992-2000); Kozbor et al., 4 Immunol. Today 72 (1983); Current Protocols in Molecular Bio. (Ausubel et al., eds., Wiley Interscience, NY, 1987-2000); Muller, 92 Meth. Enzymol. 589 (1983).

Such antibodies optionally further affect a specific ligand, such as where such antibody modulates, decreases, increases, antagonizes, angonizes, mitigates, aleviates, blocks, inhibits, abrogates and/or interferes with at least one EBV-associated activity or binding in vitro, in situ and/or in vivo. As a non-limiting example, a suitable EBV antibody, specified portion or variant of the present invention can bind at least one EBV antigen, or specified portions, variants or domains thereof, and neutralize the EBV infectivity. A suitable EBV antibody, specified portion, or variant can also optionally affect at least one of EBV activity or function, such as but not limited to, RNA, DNA or protein synthesis, viral packaging, or budding.

Traditionally, monoclonal antibodies have been produced as native molecules in murine hybridoma lines. In addition to that technology, the present invention provides for recombinant DNA expression of monoclonal antibodies. This allows the production of humanized antibodies as well as a spectrum of antibody derivatives and fusion proteins in a host species of choice. More recently, the production of antibodies in bacteria, yeast, transgenic animals and chicken eggs have emerged as promising alternatives for hybridoma-based production systems. The main advantages of transgenic animals are potential high yields from renewable sources. The identity of the relevant antibody CDRs of the present invention can now allow for these advanced approaches to antibody production.

Recombinant, humanized EBV antibodies useful in the methods and compositions of the present invention can optionally be characterized by high affinity binding to EBV antigen and, optionally, having low toxicity. In particular, an antibody, specified fragment or variant of the invention, where the individual components, such as the variable region, constant region and framework, individually and/or collectively, optionally and preferably possess low immunogenicity, is useful in the present invention. The antibodies that can be used in the invention are characterized by their ability to treat patients for extended periods with measurable alleviation of symptoms and low and/or acceptable toxicity. Low or acceptable immunogenicity and/or high affinity, as well as other suitable properties, can contribute to the therapeutic results achieved. "Low immunogenicity" is defined herein as raising significant HAHA, HACA or HAMA responses in less than about 75%, or preferably less than about 50% of the patients treated and/or raising low titers in the patient treated (less than about 300, preferably less than about 100 measured with a double antigen enzyme immunoassay). Elliott et al., 344 Lancet 1125 (1994).

Human antibodies that are specific for EBV envelope components or viral capsid proteins or portions thereof, e.g., gp350, can be raised against an appropriate immunogenic antigen, such as isolated and/or EBV glycoprotein, protein or a portion thereof (including synthetic molecules, such as synthetic peptides), with reference to the antibodies of the present invention. Other specific or general mammalian antibodies can be raised similarly. Preparation of immunogenic EBV antigens, and monoclonal antibody production can be performed using any suitable technique.

An embodiment of the present invention provides for a cell line that produces a recombinant, humanized monoclonal antibody that has a high degree of specificity and affinity towards an EBV antigen, particularly EBV gp350. The present invention relates also to variants and mutants of antibody-expressing cell lines that occur spontaneously or that can be produced artificially using known methods and that retain the characteristic properties of the starting material, that is to say are still capable of producing the antibodies according to the invention or derivatives thereof. The present invention also includes methods for the production of said cell lines and to methods for the production of said monoclonal antibodies. Clones and sub-clones of cell lines are to be understood as being produced from the starting clone by repeated cloning and that still have the features of the starting clone that are essential to the invention.

More specifically, nucleic acid, protein or peptide molecules of the invention may be utilized to develop antibodies that bind EBV gp350. For preparation of the gp350-binding antibodies of the present invention, any technique which provides for the production of antibody molecules by continuous cell lines in culture may be used. See, e.g., Kohler & Milstein, 256 Nature 495 (1975), U.S. Pat. No. 4,376,110; Ausubel et al., 1988; Curr. Prot. Immunol. (Colligan et al., eds., Greene Pub. Assoc. & Wiley Interscience NY, 1992-1996); U.S. Pat. No. 6,245,898; U.S. Patent Pub. No. 2010/0129318. Other suitable methods of producing or isolating antibodies of the requisite specificity can be used, including, but not limited to, methods that select recombinant antibody from a peptide or protein library (e.g., a bacteriophage, ribosome, oligonucleotide, RNA, cDNA, or the like, display library) as commercially available, or that rely upon immunization of transgenic animals (e.g., SCID mice), that are capable of producing a repertoire of human antibodies, as known in the art and/or as described herein. Such techniques, include, but are not limited to, ribosome display; single cell antibody producing technologies (e.g., selected lymphocyte antibody method ("SLAM"); gel microdroplet and flow cytometry; or B-cell selection. See, e.g., U.S. Pat. No. 7,829,678; U.S. Patent Pub. No. 2010/0129318 (and references cited therein).

The recombinant, humanized EBV-neutralizing antibodies of the present invention can be optionally produced by a cell line, a mixed cell line, an immortalized cell or clonal population of immortalized cells, as well known in the art. See, e.g., Current Protocols in Molecular Bio. (Ausubel et al., eds., John Wiley & Sons, Inc., NY, 1987-2001); Sambrook et al., Molecular Cloning: Lab. Manual (2nd edition, Cold Spring Harbor, N.Y., 1989); Harlow & Lane, Antibodies, Lab. Manual (Cold Spring Harbor, N.Y., 1989); Current Protocols in Immunology (Colligan et al., eds., John Wiley & Sons, Inc., NY, 1994-2001); Colligan et al., Current Protocols in Protein Sci. (John Wiley & Sons, NY, 1997-2001); Ou et al., 145 J. Immun. Meths. 111 (1991); U.S. Pat. No. 7,829,678.

Methods for engineering or humanizing non-human or human antibodies can also be used and are well known in the art. Generally, a humanized or engineered antibody has one or more amino acid residues from a source which is non-human, e.g., but not limited to mouse, rat, rabbit, non-human primate or other mammal. These human amino acid residues are often referred to as "import" residues, which are typically taken from an "import" variable, constant or other domain of a known human sequence. Known human Ig sequences are disclosed and available from publically accessible data bases through the National Center for Biotechnology Information at the National Institutes of Health, the American Type Culture Collection, many major universities, and the like, and references such as Kabat et al., Sequences of Proteins of Immunological Interest, U.S. Dept. Health (1983). In a particular embodiment of the present invention, murine variable regions are included on imported human Fc regions.

In another particular embodiment, murine CDRs are included on imported human framework amino acid sequences within the variable region. Thus, for example, a recombinant humanized EBV neutralizing antibody comprises CDR H1 with amino acids GSSFTDYT (SEQ ID NO:5), CDR H2 with amino acids INPYNGGT (SEQ ID NO:6), CDR H3 with amino acids AGGLRRVNWFAY (SEQ ID NO:7), CDR L1 with amino acids TGAVTTSNY (SEQ ID NO:14), CDR L2 with amino acids GTN (SEQ ID NO:15), CDR L3 with amino acids VLWHSNHWV (SEQ ID NO:16), and human framework regions between the CDRs (e.g., substitution of the murine FRs, depicted in FIGS. 2 and 4, with human FRs), as well as human Fc regions.

Such human imported sequences can be used to reduce immunogenicity or reduce, enhance or modify binding, affinity, on-rate, off-rate, avidity, specificity, half-life, or any other suitable characteristic, as known in the art. Generally, part or all of the non-human or human CDR sequences are maintained while the non-human sequences of the variable and constant regions are replaced with human or other amino acids. Antibodies can also optionally be humanized with retention of high affinity for the antigen and other favorable biological properties. To achieve this goal, humanized antibodies can be prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding. Humanization or engineering of antibodies of the present invention can be performed using any known method. See, e.g., U.S. Patent Pub. No. 2010/0129318; U.S. Pat. No. 7,829,678, and references cited therein.

Indeed, given the identification of the EBV-neutralizing CDRs presented herein, a fully humanized antibody can be designed and produced by any one of several commercial entities, such as Creative Biolabs (Shirley, N.Y.), Avant Gen, Inc. (San Diego, Calif.), or LakePharma, Inc. (Belmont, Calif.).

Screening antibodies for specific binding to similar proteins or fragments can be conveniently achieved using peptide display libraries. This method involves the screening of large collections of peptides for individual members having the desired function or structure. Antibody screening of peptide display libraries is well known in the art. The displayed peptide sequences can be from 3 to 5000 or more amino acids in length, frequently from 5-100 amino acids long, and often from about 8 to 25 amino acids long. In addition to direct chemical synthetic methods for generating peptide libraries, several recombinant DNA methods have been described. One type involves the display of a peptide sequence on the surface of a bacteriophage or cell. Each bacteriophage or cell contains the nucleotide sequence encoding the particular displayed peptide sequence. Other systems for generating libraries of peptides have aspects of both in vitro chemical synthesis and recombinant methods. See, e.g., U.S. Patent Pub. No. 2010/0129318 (and references cited therein). Peptide display libraries, vector, and screening kits are commercially available from such suppliers as Invitrogen (Carlsbad, Calif.), and Cambridge antibody Technologies (Cambridgeshire, UK). See also U.S. Patent Pub. No. 2010/0129318; U.S. Pat. No. 7,829,678.

The present invention accordingly encompasses the expression of a recombinant, humanized EBV-neutralizing antibody in either prokaryotic or eukaryotic cells. Suitable hosts include bacterial or eukaryotic hosts including bacteria, yeast, insects, fungi, bird and mammalian cells either in vivo, or in situ, or host cells of mammalian, insect, bird or yeast origin. Mammalian cells provide post-translational modifications to immunoglobulin protein molecules including leader peptide removal, folding and assembly of H and L chains, glycosylation of the antibody molecules, and secretion of functional antibody protein. The mammalian cell or tissue may be of human, primate, hamster, rabbit, rodent, cow, pig, sheep, horse, goat, dog or cat origin, but any other mammalian cell may be used. Mammalian cells, which can be useful as hosts for the production of antibody proteins, in addition to the cells of lymphoid origin described above, include cells of fibroblast origin, such as Vero (ATCC CRL 81) or CHO-K1 (ATCC CRL 61) cells. The CHO cells used for expression of the antibodies according to the invention may be dihydrofolate reductase (dhfr) deficient and so dependent on thymidine and hypoxanthine for growth. See Urlaub et al., 77 PNAS 4216 (1980). Another expression system for use with CHO or myeloma cells is the glutamine synthetase (GS) amplification system described in, for example, U.S. Pat. No. 5,122,464. Antibodies of the present invention can also be prepared using a gp350 antibody-encoding nucleic acid to provide transgenic animals or mammals, such as goats, cows, horses, sheep, and the like, that produce such antibodies in their milk. Such animals can be provided using known methods. See, e.g., U.S. Pat. No. 5,827,690; U.S. Pat. No. 5,849,992; U.S. Pat. No. 4,873,316; U.S. Pat. No. 5,849,992; U.S. Pat. No. 5,994,616; U.S. Pat. No. 5,565,362; U.S. Pat. No. 5,304,489.

Antibodies of the present invention can also be prepared using a gp350 antibody encoding nucleic acid to provide transgenic plants and cultured plant cells (e.g., but not limited to tobacco and maize) that produce such antibodies, specified portions or variants in the plant parts or in cells cultured therefrom. In plant culture, as well as in some animal or animal cell-based cultures, genetic removal of glycosylation sites within the antibody compensates for variant glycosylations of these hosts that may negatively impact immunogenicity or clearance in humans. See, e.g., U.S. Pat. No. 6,140,075; WO 2001/029242; WO 1998/010062. Additionally, production of recombinant EBV-neutralizing antibodies or functional derivatives thereof in insects can be achieved, for example, by infecting the insect host with a baculovirus engineered to express a transmembrane polypeptide by methods known to those of skill See Ausubel et al., 1987, 1993.

The antibodies of the invention can bind EBV-neutralizing epitopes, e.g., gp350, with a wide range of affinities (KD). In a preferred embodiment, at least one human mAb of the present invention can optionally bind EBV with high affinity. For example, a human mAb can bind EBV gp350 with a KD equal to or less than about $10^{-7}$ M, such as but not limited to, 0.1-9.9, inclusive x $10^{-7}$, $10^{-8}$, $10^{-9}$, $10^{-10}$, $10^{-11}$, $10^{-12}$, or $10^{-13}$, inclusive. The affinity or avidity of an antibody for an antigen can be determined experimentally using any suitable method. The measured affinity of a particular antibody-antigen interaction can vary if measured under different conditions (e.g., salt concentration, pH). Thus, measurements of affinity and other antigen-binding parameters (e.g., KD, Ka, Kd) are preferably made with standardized solutions of antibody and antigen, and a standardized buffer, such as the buffer described herein.

Also provided is an isolated nucleic acid that encodes least one isolated recombinant, humanized, EBV-neutralizing antibody, an isolated nucleic acid vector comprising the isolated nucleic acid, and/or a prokaryotic or eukaryotic host cell comprising the isolated nucleic acid. The host cell can optionally be at least one selected from prokaryotic or eukaryotic cells, or fusion cells thereof, e.g., but not limited to, mammalian, plant or insect, such as but not limited to, CHO, myeloma, or lymphoma cells, bacterial cells, yeast cells, silk worm cells, or any derivative, immortalized or transformed cell thereof. Also provided is a method for producing at least one recombinant, humanized EBV-neutralizing antibody, comprising translating the antibody encoding nucleic acid under conditions in vitro, in vivo or in situ, such that the antibody is expressed in detectable or recoverable amounts.

The humanized, recombinant, neutralizing antibody of the present invention may be purified. "Purification" involves removal of a substance from surrounding impurities without changing the substance itself. "Isolation," as applied to DNA, refers to chemical manipulation—cleavage of covalent bonds—that produces a molecule that is different from one found in nature. In that regard, the present invention also provides for isolated DNAs that encode for the antibodies described herein.

Although occasionally an amino acid sequence can be encoded by only a single oligonucleotide, frequently the amino acid sequence can be encoded by any of a set of similar oligonucleotides. Importantly, whereas all of the members of this set contain oligonucleotides which are capable of encoding the peptide fragment and, thus, potentially contain the same oligonucleotide sequence as the gene which encodes the peptide, only one member of the set contains the nucleotide sequence that is identical to the nucleotide sequence of the gene. Because this member is present within the set, and is capable of hybridizing to DNA even in the presence of the other members of the set, it is possible to employ the unfractionated set of oligonucleotides in the same manner in which one would employ a single oligonucleotide to clone the gene that encodes the protein.

The oligonucleotide, or set of oligonucleotides, containing the theoretical "most probable" sequence capable of encoding a humanized EBV-neutralizing antibody including a variable or constant region as described herein is used to identify the sequence of a complementary oligonucleotide or set of oligo-nucleotides which is capable of hybridizing to the "most probable" sequence, or set of sequences. An oligonucleotide containing such a complementary sequence can be employed as a probe to identify and isolate the variable or constant region anti-EBV antibody or antigen-binding peptide gene (Sambrook et al., 1989).

A suitable oligonucleotide, or set of oligonucleotides, which is capable of encoding a peptide that neutralized EBV via antigen-binding (or which is complementary to such an oligonucleotide, or set of oligonucleotides) is identified, synthesized, and hybridized by means well known in the art, against a DNA or a cDNA preparation derived from cells which are capable of expressing anti-EBV antibodies or variable or constant regions thereof. Single stranded oligonucleotide molecules complementary to the "most probable" anti-EBV region peptide coding sequences can be synthesized using procedures which are well known to those of ordinary skill in the art. See Belagaje et al., 254 J. Biol. Chem. 5765 (1979); Maniatis et al., in Molec. Mech. in Control of Gene Expression (Nierlich et al., eds., Acad. Press, NY, 1976); Wu et al., 1978; Khorana, 203 Science 614 (1979).

Additionally, DNA synthesis can be achieved through the use of automated synthesizers. Techniques of nucleic acid hybridization are disclosed by Sambrook et al., 1989, and by Haynes et al., in Nucleic Acid Hybridization, Practical Approach (IRL Press, DC, 1985). Hybridization wash conditions can include wash solution of 0.2×SSC/0.1% SDS and incubation with rotation for 10 minutes at room temperature, (low stringency wash), wash solution of prewarmed (42° C.) 0.2×SSC/0.1% SDS and incubation with rotation for fifteen minutes at 42° C. (medium stringency wash) and wash solution of prewarmed (68° C.) 0.1×SSC/0.1% SDS and incubation with rotation for fifteen minutes at 68° C. (high stringency wash). See Antibodies: Lab. Manual (Harlow & Lane eds., Cold Spring Harbor Lab., NY, 1988). Techniques such as, or similar to, those described above have successfully enabled the cloning of genes for human aldehyde dehydrogenases (Hsu et al., 82 PNAS 3771 (1985)), fibronectin (Suzuki et al., 4 Bur. Mol. Biol. Organ. J. 2519 (1985)), the human estrogen receptor gene (Walter et al., 82 PNAS 7889 (1985)), tissue-type plasminogen activator (Pennica et al., 301 Nature 214 (1983)) and human term placental alkaline phosphatase complementary DNA (Keun et al., 82 PNAS 8715 (1985)).

It is also intended that the antibody coding regions for use in the present invention could also be provided by altering existing antibody genes using standard molecular biological techniques that result in variants (agonists) of the antibodies described herein. Such variants include, but are not limited to deletions, additions and substitutions in the amino acid sequence of the anti-EBV antibodies or peptides disclosed herein.

For example, one class of substitutions is conserved amino acid substitutions. Such substitutions are those that substitute a given amino acid in an anti-EBV antibody peptide by another amino acid of like characteristics. Typically seen as conservative substitutions are the replacements, one for another, among the aliphatic amino acids Ala, Val, Leu, and Ile; interchange of the hydroxyl residues Ser and Thr, exchange of the acidic residues Asp and Glu, substitution between the amide residues Asn and Gln, exchange of the basic residues Lys and Arg, replacements among the aromatic residues Phe, Tyr, and the like. Guidance concerning which amino acid changes are likely to be phenotypically silent is found in Bowie et al., 247 Science 1306 (1990).

Variant or agonist anti-EBV antibodies may be fully functional or may lack function in one or more activities. Fully functional variants typically contain only conservative variations or variations in non-critical residues or in non-critical regions. For example, the amino acid residues in CDR L3, GTN (SEQ ID NO: 15), could be substituted with the amino acids GTQ, DTQ, DTN, GSN, GSQ, or DSQ, and the binding of the antibody compared as known in the art. Functional variants can also contain substitution of similar amino acids that result in no change or an insignificant change in function. Alternatively, such substitutions may positively or negatively affect function to some degree. Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis. Cunningham et al., 244 Sci. 1081 (1989). The latter procedure introduces single alanine mutations at every residue in the molecule. The resulting mutant molecules are then tested for biological activity such as epitope binding or in vitro ADCC activity. Sites that are critical for ligand-receptor binding can also be determined by structural analysis such as crystallography, nuclear magnetic resonance, or photoaffinity labeling. Smith et al., 224 J. Mol. Biol. 899 (1992); de Vos et al., 255 Sci. 306 (1992).

Moreover, polypeptides often contain amino acids other than the twenty "naturally occurring" amino acids. Further, many amino acids, including the terminal amino acids, may be modified by natural processes, such as processing and other post-translational modifications, or by chemical modification techniques well known in the art. Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, de-glycosylation, lipid attachment, sulfation, gamma-carboxylation of glutamic acid residues, hydroxylation and ADP-ribosylation, for instance, are described in most basic texts, such as Proteins: Structure & Molecular Prop. (2nd ed., Creighton, W.H. Freeman & Co., NY, 1993). Many detailed reviews are available on this subject, such as by Wold, Posttranslational Covalent Modification of Proteins (Johnson, ed., Academic Press, NY, 1983); Seifter et al. 182 Meth. Enzymol. 626 (1990); Rattan et al. 663 Ann. NY Acad. Sci. 48 (1992).

Accordingly, the antibodies of the present invention also encompass derivatives or analogs in which a substituted amino acid residue is not one encoded by the genetic code, in which a substituent group is included pegylation as mentioned previously. Similarly, the additions and substitutions in the amino acid sequence as well as variations, and modifications just described may be equally applicable to the amino acid sequence of the EBV antigen and/or epitope or peptides thereof, and are thus encompassed by the present invention. As mentioned above, the genes encoding the recombinant, humanized monoclonal antibody according to the present invention is specifically effective in the neutralization of EBV.

As noted, the antibodies of the present invention include chimeric antibodies comprising part human and part mouse antibodies, in which the constant region from human antibodies are cloned to a variable regions of light and heavy chains from murine-derived antibody. See FIGS. 1 and 3. In some instances, 70% of the human sequences are retained. Humanized antibodies are chimeric antibodies in which perhaps 90% of the human antibody framework is retained, and combined only with the murine the complementary determining regions. Fully humanized antibodies are also contemplated in the present invention.

Recombinant murine or chimeric murine-human or human-human antibodies that bind an epitope included in the amino acid residues of EBV, e.g., gp350, can be provided according to the present invention using known techniques based on the teaching provided herein. See, e.g., Ausubel et al., 1987, 1992, and 1993; Sambrook et al., 1989. For example, an antibody may be humanized by grafting the desired CDRs onto a human framework. See EP0239400; U.S. Pat. No. 7,829,678. Thus, in one embodiment, a fused chimeric gene is created which comprises a first DNA segment that encodes at least the antigen-binding region of non-human origin, such as a functionally rearranged V region with joining (J) segment, linked to a second DNA segment encoding at least a part of a human C region. "Fully humanized antibodies" against EBV are also contemplated in the present invention. Fully humanized antibodies are molecules containing both the variable and constant region of the human immunoglobulin. See, e.g., U.S. Pat. No. 7,829,678, U.S. Pat. No. 7,276,239 and U.S. Pat. No. 6,835,823; Ruguska et al., 9 Prot. Engin. 895 (1996).

Additionally, a recombinant humanized antibody may be further optimized to decrease potential immunogenicity, while maintaining functional activity, for therapy in humans. In this regard, functional activity means a polypeptide capable of displaying one or more known functional activities associated with an EBV-neutralizing antibody of the invention. Such functional activities include, biological activity, and ability to bind to a ligand for an EBV polypeptide. Additionally, a polypeptide having functional activity means the polypeptide exhibits activity similar, but not necessarily identical to, an activity of an EBV-neutralizing antibody of the present invention, including mature forms, as measured in a particular assay, such as, for example, a biological assay, with or without dose dependency. In the case where dose dependency does exist, it need not be identical to that of the anti-EBV antibodies, but rather substantially similar to the dose-dependence in a given activity as compared to the antibodies of the present invention (i.e., the candidate polypeptide will exhibit greater activity, or not more than about 25-fold less, about 10-fold less, or about 3-fold less activity relative to the EBV-neutralizing antibodies of the present invention). See, e.g., Roguska et al., 10 Protein Engin. 181 (1997).

Once expressed, the whole antibodies, their dimers, individual light and heavy chains, or other immunoglobulin forms of the present EBV-neutralizing antibodies can be recovered and purified by known techniques, e.g., immunoabsorption or immunoaffinity chromatography, chromatographic methods such as HPLC (high performance liquid chromatography), ammonium sulfate precipitation, gel electrophoresis, or any combination of these. See generally, Scopes, Protein Purification (Springer-Verlag, NY, 1982). Substantially pure immunoglobulins of at least about 90% to 95% homogeneity are advantageous, as are those with 98% to 99% or more homogeneity, particularly for pharmaceutical uses. Once purified, partially or to homogeneity as desired, a humanized antibody may then be used therapeutically or in developing and performing assay procedures, immunofluorescent stainings, and the like. See generally, Vols. I & II Immunol. Meth. (Lefkovits & Pernis, eds., Acad. Press, NY, 1979, 1981).

Along with the above production techniques, in vitro systems such as phage display methods of fully human antibodies and antibody peptides, many of the benefits of human antibodies as both diagnostics and therapeutics are now being realized. See, e.g., U.S. Pat. No. 7,829,678.

Another ligand binding molecule that may be constructed from the DNA sequence information contained herein, and the associated knowledge gained about the PCAA epitopes provided by the invention herein, involves the construction of ANTICALINS® lipocalins, a widespread group of small and robust proteins that are usually involved in the physiological transport or storage of chemically sensitive or insoluble compounds. ANTICALINS® lipocalins have been engineered that recognize hapten-like compounds, peptides, and protein targets, e.g. extracellular domains of cell surface receptors. See Schlehuber & Skerra, 19 BioDrugs 279 (2005). Fusion proteins with enzymes and also bispecific binding proteins (so-called DUOCALINS® bispecific binding proteins, Pieris AG, Freising-Weihenstephan, Germany) have also been successfully prepared. Pre-clinical experiments have been conducted. See, e.g., Komdorfer et al., 330 J. Mol. Biol. 385 (2003).

Another antibody type with application to the invention described herein includes the camilid immunoglobulins which possess functional heavy chains and lack light chains. These antibodies are assembled from dedicated V and C gamma genes. They have been cloned and adapted using phage display technology to produce antigen-specific single-domain antibody fragments with intrinsic high stability. See U.S. Patent Appl. Pub. No. 2003/0088074.

Another relevant derivative takes advantage of new technology for providing bacterially produced antibody fragments that can crosslink antigen and antibody effector molecules (Fc-region molecules), called PEPBODIES®. antibody fragments. See U.S. Patent Appl. Pub. No. 2004/0101905. Hence, the binding molecules comprising the antigen binding site of the anti-PCAA site is genetically fused to peptides that display one or more of the effector functions associated with the Fc-region, and provides for functions such as interaction with cell receptors and complement activation.

The new antigen receptor (IgNAR) molecules from sharks may also be considered a "derivative" antibody molecule. The NAR is a disulphide bonded dimer of two protein chains, each containing one variable and five constant domains, and functions as an antibody. Nuttall et al., 270 Eur. J. Biochem., 3543 (2003). The sequences of the PCAA-binding antibody of the present invention may be constructed into the NAR variable region to create an in vitro library incorporating synthetic the CDR regions. This results in a single domain binding reagent.

A "derivative" of an antibody contains additional chemical moieties not normally a part of the protein. Covalent modifications of the protein are included within the scope of this invention. Such modifications may be introduced into the molecule by reacting targeted amino acid residues of the antibody with an organic derivatizing agent that is capable of reacting with selected side chains or terminal residues. For example, derivatization with bifunctional agents, well-known in the art, is useful for cross-linking the antibody or fragment to a water-insoluble support matrix or to other macromolecular carriers.

Derivatives also include radioactively labeled monoclonal antibodies that are labeled. For example, with radioactive iodine (125I, 131I), carbon (14C), sulfur (35S), indium (111In), tritium (3H) or the like; conjugates of monoclonal antibodies with biotin or avidin, with enzymes, such as horseradish peroxidase, alkaline phosphatase, β-D-galactosidase, glucose oxidase, glucoamylase, carboxylic acid anhydrase, acetylcholine esterase, lysozyme, malate dehydrogenase or glucose 6-phosphate dehydrogenase; and also conjugates of monoclonal antibodies with bioluminescent agents (such as luciferase), chemoluminescent agents (such as acridine esters) or fluorescent agents (such as phycobiliproteins). An example of a derivative of the antibody of the invention is an antibody-small molecule drug conjugate, such as an antibody-maytansinoid conjugate, that displays cytotoxic activity. See U.S. Patent Appl. Pub. No. 2004/0039176. Preclinical evaluation has shown that this conjugate acts as a tumor-activated prodrug that exhibits potent antitumor activity in xenograft models. Further cytotoxic antibody derivatives are discussed below.

Another derivative bifunctional antibody of the present invention is a bispecific antibody, generated by combining parts of two separate antibodies that recognize two different antigenic groups. This may be achieved by crosslinking or recombinant techniques. Additionally, moieties may be added to the antibody or a portion thereof to increase half-life in vivo (e.g., by lengthening the time to clearance from the blood stream. Such techniques include, for example, adding PEG moieties (also termed pegilation), and are well-known in the art. See U.S. Patent. Appl. Pub. No. 2003/0031671.

Structural analogs of EBV-neutralizing antibodies and peptides of the present invention are provided by known method steps based on the teaching and guidance presented herein. Knowledge of the three-dimensional structures of proteins is crucial in understanding how they function. The three-dimensional structures of hundreds of proteins are currently available in protein structure databases (in contrast to the thousands of known protein sequences in sequence databases). Analysis of these structures shows that they fall into recognizable classes of motifs. It is thus possible to model a three-dimensional structure of a protein based on the protein's homology to a related protein of known structure. Many examples are known where two proteins that have relatively low sequence homology, can have very similar three dimensional structures or motifs.

In recent years it has become possible to determine the three dimensional structures of proteins of up to about 15 kDa by nuclear magnetic resonance (NMR). The technique requires a concentrated solution of pure protein: no crystals or isomorphous derivatives are needed. The structures of a number of proteins have been determined by this method. The details of NMR structure determination are well-known in the art. See, e.g., Wuthrich, NMR Proteins & Nucleic ACIDScids (Wiley, N.Y., 1986); Wuthrich, 243 Science 45 (1989); Clore et al., 24 Critical Rev. Biochem. Molec. Biol. 479 (1989); Cooke et al., 8 Bioassays 52 (1988).

In applying this approach, a variety of 1H NMR 2D data sets are collected for anti-EBV antibodies of the present invention. One type of analysis, COSY (Correlated Spectroscopy) identifies proton resonances that are linked by chemical bonds. These spectra provide information on protons that are linked by three or less covalent bonds. NOESY (nuclear Overhauser enhancement spectroscopy) identifies protons which are close in space (less than 0.5 nm). Following assignment of the complete spin system, the secondary structure is defined by NOESY. Cross peaks (nuclear Overhauser effects or NOE's) are found between residues that are adjacent in the primary sequence of the peptide and can be seen for protons less than 0.5 nm apart. The data gathered from sequential NOE's combined with amide proton coupling constants and NOE's from non-adjacent amino acids that are adjacent to the secondary structure, are used to characterize the secondary structure of the peptides. Aside from predicting secondary structure, NOE's indicate the distance that protons are in space in both the primary amino acid sequence and the secondary structures. Tertiary structure predictions are determined, after all the data are considered, by a "best fit" extrapolation.

Types of amino acids are first identified using through-bond connectivities. Next, specific amino acids are assigned using through-space connectivities to neighboring residues, together with the known amino acid sequence. Structural information is then tabulated and is of three main kinds: The NOE identifies pairs of protons which are close in space, coupling constants give information on dihedral angles and slowly exchanging amide protons give information on the position of hydrogen bonds. The restraints are used to compute the structure using a distance geometry type of calculation followed by refinement using restrained molecular dynamics. The output of these computer programs is a family of structures which are compatible with the experimental data (i.e. the set of pairwise <0.5 nm distance restraints). The better that the structure is defined by the data, the better the family of structures can be superimposed, (i.e., the better the resolution of the structure). In the better defined structures using NMR, the position of much of the backbone (i.e. the amide, Cα and carbonyl atoms) and the side chains of those amino acids that lie buried in the core of the molecule can be defined as clearly as in structures obtained by crystallography. The side chains of amino acid residues exposed on the surface are frequently less well defined, however. This probably reflects the fact that these surface residues are more mobile and can have no fixed position. (In a crystal structure this might be seen as diffuse electron density).

Thus, according to the present invention, use of NMR spectroscopic data is combined with computer modeling to arrive at structural analogs of at least portions of EBV-neutralizing antibodies and peptides based on a structural understanding of the topography. Using this information, one of ordinary skill in the art will know how to achieve structural analogs of anti-EBV antibodies, such as by rationally-based amino acid substitutions allowing the production of peptides in which the EBV binding affinity or avidity is modulated in accordance with the requirements of the expected therapeutic or diagnostic use of the molecule, for example, the achievement of greater specificity for EBV binding.

Alternatively, compounds having the structural and chemical features suitable as anti-EBV therapeutics and diagnostics provide structural analogs with selective EBV affinity, Molecular modeling studies of EBV-binding compounds, such as EBV receptors, anti-EBV antibodies, or other EBV-binding molecules, using a program such as MacroModel® (Schrodinger, LLC, NY), Insight®II and Discover® (Accelrys Software Inc., Burlington, Mass.), provide such spatial requirements and orientation of the anti-EBV antibodies according to the present invention. Such structural analogs of the present invention thus provide selective qualitative and quantitative anti-EBV activity in vitro, in situ and/or in vivo.

In some embodiments, the technology described herein relates to a nucleic acid encoding an antibody or antigen-binding portion thereof as described herein. As used herein, the term "nucleic acid" or "nucleic acid sequence" refers to a polymeric molecule incorporating units of ribonucleic acid, deoxyribonucleic acid or an analog thereof. The nucleic acid can be either single-stranded or double-stranded. A single-stranded nucleic acid can be one strand nucleic acid of a denatured double-stranded DNA.

Nucleic acid molecules encoding amino acid sequence variants of antibodies are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody. A nucleic acid sequence encoding at least one antibody, portion or polypeptide as described herein can be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed, e.g., by Maniatis et al., Molecular Cloning, Lab. Manual (Cold Spring Harbor Lab. Press, NY, 1982 and 1989), and Ausubel, 1987, 1993, and can be used to construct nucleic acid sequences which encode a monoclonal antibody molecule or antigen binding region thereof.

In some embodiments, a nucleic acid encoding an antibody or antigen-binding portion thereof as described herein is comprised by a vector. In some of the aspects described herein, a nucleic acid sequence encoding an antibody or antigen-binding portion thereof as described herein, or any module thereof, is operably linked to a vector. The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, chromosome, virus, virion, etc.

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification. The term "expression" refers to the cellular processes involved in producing RNA and proteins and as appropriate, secreting proteins, including where applicable, but not limited to, for example, transcription, transcript processing, translation and protein folding, modification and processing. "Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g. 5' untranslated (5'UTR) or "leader" sequences and 3' UTR or "trailer" sequences, as well as intervening sequences (introns) between individual coding segments (exons).

As used herein, the term "viral vector" refers to a nucleic acid vector construct that includes at least one element of viral origin and has the capacity to be packaged into a viral vector particle. The viral vector can contain the nucleic acid encoding an antibody or antigen-binding portion thereof as described herein in place of non-essential viral genes. The vector and/or particle may be utilized for the purpose of transferring any nucleic acids into cells either in vitro or in vivo. Numerous forms of viral vectors are known in the art.

By "recombinant vector" is meant a vector that includes a heterologous nucleic acid sequence, or "transgene" that is capable of expression in vivo. It should be understood that the vectors described herein can, in some embodiments, be combined with other suitable compositions and therapies. In some embodiments, the vector is episomal. The use of a suitable episomal vector provides a means of maintaining the nucleotide of interest in the subject in high copy number extra chromosomal DNA thereby eliminating potential effects of chromosomal integration.

In some embodiments, the nucleic acid encoding an antibody or antigen-binding fragment thereof as described herein can be comprised by a vector. Such methods allow clinicians to introduce a nucleic acid sequence encoding an antibody or antigen-binding fragment thereof as described herein directly into a patient (in vivo gene therapy) or into cells isolated from a patient or a donor (ex vivo gene therapy). The antibodies and antigen-binding fragments thereof described herein, when produced by transduced cells after gene therapy, can be maintained at a relatively constant level in a subject, as compared to a protein that is administered directly. Such sustained production of an antibody or antigen-binding fragment thereof is particularly appropriate in the treatment of chronic diseases. Expression can be transient (on the order of hours to weeks) or sustained (weeks to months or longer), depending upon the specific construct used and the target tissue or cell type. These transgenes can be introduced as a linear construct, a circular plasmid, or a viral vector, which can be an integrating or non-integrating vector. The transgene can also be constructed to permit it to be inherited as an extrachromosomal plasmid (Gassmann, et al., Proc. Natl. Acad. Sci. USA (1995) 92:1292). Further, regulatable genetic constructs using small molecule inducers have been developed that can be included in vectors to be used in some embodiments of the present invention described herein. (Rivera et al. (1996) Nat. Med. 2:1028-32; No et al. (1996) Proc. Natl. Acad. Sci. USA, 93:3346-51; Gossen and Bujard (1992) Proc. Natl. Acad. Sci. USA 89:5547-51; the GeneSwitch® system (Valentis, Inc., Burlingame, Calif.)). These systems are based on the use of engineered transcription factors the activity of which is controlled by a small molecule drug, and a transgene, the expression of which is driven by the regulated transcription factor (Rivera et al. (1996) Nat. Med. 2:1028-32; Pollock et al. (2000) Proc. Natl. Acad. Sci. USA 97:13221-26; U.S. Pat. Nos. 6,043,082 and 6,649,595; Rivera et al. (1999) Proc. Natl. Acad. Sci. USA 96:8657-62). In some of the aspects described herein, a nucleic acid sequence encoding antibody or antigen-binding fragment thereof as described herein is operably linked to a vector. Vectors can include cloning and expression vehicles, as well as viral vectors. By "recombinant vector" is meant a vector that includes a heterologous nucleic acid sequence, or "transgene" that is capable of expression in vivo. It should be understood that the vectors described herein can, in some embodiments, be combined with other suitable compositions and therapies. Vectors useful for the delivery of a sequence encoding an antibody or antigen-binding fragment thereof as described herein can include one or more regulatory elements (e.g., promoter, enhancer, etc.) sufficient for expression of the antibody or antigen-binding fragment thereof in the desired target cell or tissue. The regulatory elements can be chosen to provide either constitutive or regulated/inducible expression. Examples of vectors useful in delivery of nucleic acids encoding an antibody or antigen-binding fragment thereof as described herein include plasmid vectors, non-viral plasmid vectors (e.g. see U.S. Pat. Nos. 6,413,942, 6,214,804, 5,580,859, 5,589,466, 5,763,270 and 5,693,622, all of which are incorporated herein by reference in their entireties); retroviruses (e.g. see U.S. Pat. No. 5,219,740; Miller and Rosman (1989) BioTechniques 7:980-90; Miller, A. D. (1990) Human Gene Therapy 1:5-14; Scarpa et al. (1991) Virology 180:849-52; Miller et al., Meth. Enzymol. 217:581-599 (1993); Burns et al. (1993) Proc. Natl. Acad. Sci. USA 90:8033-37; Boris-Lawrie and Temin (1993) Curr. Opin. Genet. Develop. 3:102-09. Boesen et al., Biotherapy 6:291-302 (1994); Clowes et al., J. Clin. Invest. 93:644-651 (1994); Kiem et al., Blood 83:1467-1473 (1994); Salmons and Gunzberg, Human Gene Therapy 4:129-141 (1993); and Grossman and Wilson, Curr. Opin. in Genetics and Devel. 3:110-114 (1993), the contents of each of which are herein incorporated by reference in their entireties); lentiviruses (e.g., see U.S. Pat. Nos. 6,143,520; 5,665,557; and 5,981,276, the contents of which are herein incorporated by reference in their entireties; adenovirus-based expression vectors (e.g., see Haj-Ahmad and Graham (1986) J. Virol. 57:267-74; Bett et al. (1993) J. Virol. 67:5911-21; Mittereder et al. (1994) Human Gene Therapy 5:717-29; Seth et al. (1994) J. Virol. 68:933-40; Barr et al. (1994) Gene Therapy 1:51-58; Berkner, K. L. (1988) BioTechniques 6:616-29; and Rich et al. (1993) Human Gene Therapy 4:461-76; Wu et al. (2001) Anesthes. 94:1119-32; Parks (2000) Clin. Genet. 58:1-11; Tsai et al. (2000) Curr. Opin. Mol. Ther. 2:515-23; and U.S. Pat. Nos. 6,048,551; 6,306,652 and 6,306,652, incorporated herein by reference in their entireties); Adeno-associated viruses (AAV) (e.g. see U.S. Pat. Nos. 5,139,941; 5,622,856; 5,139,941; 6,001,650; and 6,004,797, the contents of each of which are incorporated by reference herein in their entireties); and avipox vectors (e.g. see WO 91/12882; WO 89/03429; and WO 92/03545; which are incorporated by reference herein in their entireties). Vectors can be packaged and/or delivered using liposomes (e.g., see U.S. Pat. Nos. 5,580,859, 5,549,127, 5,264,618, 5,703,055; 4,663,161 and 4,871,488; and Hug and Sleight (1991) Biochim. Biophys. Acta. 1097:1-17; Straubinger et al. (1983) in Methods of Enzymology Vol. 101, pp. 512-27; de Lima et al. (2003) Current Medicinal Chemistry, Volume 10(14): 1221-31; Papahadjopoulos et al. (1975) Biochem. Biophys. Acta. 394:483-491; all of which are incorporated by reference herein in their entireties) biolistic delivery; DEAE dextran-mediated transfection, calcium phosphate precipitation, polylysine- or polyornithine-mediated transfection, or precipitation using other insoluble inorganic salts, such as strontium phosphate, aluminum silicates including bentonite and kaolin, chromic oxide, magnesium silicate, talc, and the like. Other useful methods of transfection include electroporation, sonoporation, protoplast fusion, peptoid delivery, or microinjection. See, e.g., Sambrook et al (1989) Molecular Cloning, A Laboratory Manual, Cold Spring Harbor Laboratories, New York, for a discussion of techniques for transforming cells of interest; and Felgner, P. L. (1990) Advanced Drug Delivery Reviews 5:163-87, for a review of delivery systems useful for gene transfer. Exemplary methods of delivering DNA using electroporation are described in U.S. Pat. Nos. 6,132,419; 6,451,002, 6,418,341, 6,233,483, U.S. Patent Publication No. 2002/0146831, and International Publication No. WO/0045823, all of which are incorporated herein by reference in their entireties.

Aspects of the present invention provide for a composition comprising at least one purified, recombinant, humanized, EBV-neutralizing antibody or a nucleic acid sequence encoding a recombinant, humanized EBV-neutralizing antibody as described herein and at least one pharmaceutically acceptable carrier or diluent. The composition can optionally further comprise an effective amount of at least one compound or protein selected from at least one of a detectable label or reporter, a chemotherapeutic agent, a radiopharmaceutical, a anti-inflammatory agent, an anti-rheumatic, a muscle relaxant, a narcotic, an analgesic, an anesthetic, a sedative, a local anesthetic, a neuromuscular blocker, an antimicrobial, an antipsoriatic, an erythropoietin, an immunization, an immunoglobulin, an immunosuppressive, a hormone, a hormone replacement drug, an antidepressant, an antipsychotic, a stimulant, an asthma medication, a beta agonist, an inhaled steroid, an epinephrine or analog, a cytokine, or a cytokine antagonist.

Also provided is a method for treating a subject in need thereof. The terms "individual", "subject", and "patient" are used interchangeably and refer to a primate, such as a monkey, ape, or human. The method can optionally further comprise using an effective amount of 0.0001 mg/kg to 500 mg/kg, inclusive, of antibody. The method can optionally further comprise using the contacting or the administrating by at least one mode selected from parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal.

The method can optionally further comprise administering, prior, concurrently or after the contacting or administering, at least one composition comprising an effective amount of at least one compound or protein selected from at least one of a detectable label or reporter, a chemotherapeutic agent, a radiopharmaceutical, an anti-inflammatory agent, an anti-rheumatic, a muscle relaxant, a narcotic, an anti-inflammatory, an analgesic, an anesthetic, a sedative, a local anesthetic, a neuromuscular blocker, an antimicrobial, an antipsoriatic, an erythropoietin, an immunization, an immunoglobulin, an immunosuppressive, a hormone, a hormone replacement drug, an antidepressant, an antipsychotic, a stimulant, an asthma medication, a beta agonist, an inhaled steroid, an epinephrine or analog, a cytokine, or a cytokine antagonist.

Typically, treatment of pathologic conditions is effected by administering an effective amount or dosage of at least one EBV-neutralizing antibody composition that total, on average, a range from at least about 0.001 ng to 500 mg of EBV antibody per kilogram of patient per dose, inclusive, such as from at least about 0.1 ng to 100 mg antibody/kilogram of patient per single or multiple administration, depending upon the specific activity of contained in the composition. Alternatively, the effective serum concentration can comprise 0.0001 ng-0.05 mg/ml serum concentration per single or multiple administration. Suitable dosages are known to medical practitioners and will, of course, depend upon the particular disease state, specific activity of the composition being administered, and the particular patient undergoing treatment. In some instances, to achieve the desired therapeutic amount, it can be necessary to provide for repeated administration, i.e., repeated individual administrations of a particular monitored or metered dose, where the individual administrations are repeated until the desired daily dose or effect is achieved.

Example doses of recombinant, humanized, EBV-neutralizing antibody can optionally include 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and/or 100-500 μg or milligrams/kg/administration, or any range, value or fraction thereof, or to achieve a serum concentration of 0.1, 0.5, 0.9, 1.0, 1.1, 1.2, 1.5, 1.9, 2.0, 2.5, 2.9, 3.0, 3.5, 3.9, 4.0, 4.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 20, 12.5, 12.9, 13.0, 13.5, 13.9, 14.0, 14.5, 4.9, 5.0, 5.5., 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 12, 12.5, 12.9, 13.0, 13.5, 13.9, 14, 14.5, 15, 15.5, 15.9, 16, 16.5, 16.9, 17, 17.5, 17.9, 18, 18.5, 18.9, 19, 19.5, 19.9, 20, 20.5, 20.9, 21, 22, 23, 24, 25, 26, 27, 28, 29, 30, 35, 40, 45, 50, 55, 60, 65, 70, 75, 80, 85, 90, 96, 100, 200, 300, 400, 500, 600, 700, 800, 900, 1000, 1500, 2000, 2500, 3000, 3500, 4000, 4500, and/or 5000 ng or μg/ml serum concentration per single or multiple administration, or any range, value or fraction thereof.

Alternatively, the dosage administered can vary depending upon known factors, such as the pharmacodynamic characteristics of the particular agent, and its mode and route of administration; age, health, and weight of the recipient; nature and extent of symptoms, kind of concurrent treatment, frequency of treatment, and the effect desired. Usually a dosage of active ingredient can be about 0.1 μg to 100 milligrams per kilogram of body weight, inclusive. Ordinarily 0.0001 to 50, such as 0.001 to 10 milligrams per kilogram per administration or in sustained release form is effective to obtain desired results.

As a non-limiting example, treatment of humans or animals can be provided as a one-time or periodic dosage of at least one EBV-neutralizing antibody of the present invention 0.1 to 100 μg/kg, inclusive, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90, 100, 200, 300, 400, 500, 600, 700, 800, 900, 1000, 2000 or 3000 μg/kg, per day, or 0.1 to 100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively or additionally, at least one of week 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52, or alternatively or additionally, at least one of 1, 2, 3, 4, 5, 6, 7, 8, 9, 10, 11, 12, 13, 14, 15, 16, 17, 18, 19, or 20 years, or any combination thereof, using single, infusion or repeated doses.

Dosage forms (composition) suitable for internal administration generally contain from about 0.00001 mg to about 500 mg of active ingredient per unit or container. In these pharmaceutical compositions the active ingredient will ordinarily be present in an amount of about 0.5-99.999% by weight based on the total weight of the composition.

For parenteral administration, the antibody can be formulated as a solution, suspension, emulsion or lyophilized powder in association, or separately provided, with a pharmaceutically acceptable parenteral vehicle. Examples of such vehicles are water, saline, Ringer's solution, dextrose solution, and 1-10% human serum albumin. Liposomes and non-aqueous vehicles such as fixed oils can also be used. The vehicle or lyophilized powder can contain additives that maintain isotonicity (e.g., sodium chloride, mannitol) and chemical stability (e.g., buffers and preservatives). The formulation is sterilized by known or suitable techniques. Suitable pharmaceutical carriers are described in the most recent edition of Remington's Pharmaceutical Sciences, a standard reference text in this field.

Many known and developed modes of can be used according to the present invention for administering pharmaceutically effective amounts of recombinant, humanized, EBV-neutralizing antibody according to the present invention. For pulmonary administration EBV antibodies of the present invention can be delivered in a carrier, as a solution, emulsion, colloid, or suspension, or as a dry powder, using any of a variety of devices and methods suitable for administration by inhalation or other modes described here within or known in the art.

Formulations for parenteral administration can contain as common excipients sterile water or saline, polyalkylene glycols such as polyethylene glycol, oils of vegetable origin, hydrogenated naphthalenes and the like. Aqueous or oily suspensions for injection can be prepared by using an appropriate emulsifier or humidifier and a suspending agent, according to known methods. Agents for injection can be a non-toxic, non-orally administrable diluting agent such as aqueous solution or a sterile injectable solution or suspension in a solvent. As the usable vehicle or solvent, water, Ringer's solution, isotonic saline, etc. are allowed; as an ordinary solvent, or suspending solvent, sterile involatile oil can be used. For these purposes, any kind of involatile oil and fatty acid can be used, including natural or synthetic or semisynthetic fatty oils or fatty acids; natural or synthetic or semisynthetic mono- or di- or tri-glycerides. Parental administration is known in the art and includes, but is not limited to, conventional means of injections, a gas pressured needle-less injection device as described in U.S. Pat. No. 5,851,198, and a laser perforator device as described in U.S. Pat. No. 5,839,446.

The invention further relates to the administration of EBV-neutralizing antibody by parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal means. AnEBV-neutralizing antibody composition can be prepared for use for parenteral (subcutaneous, intramuscular or intravenous) or any other administration particularly in the form of liquid solutions or suspensions; for use in vaginal or rectal administration particularly in semisolid forms such as, but not limited to, creams and suppositories; for buccal, or sublingual administration such as, but not limited to, in the form of tablets or capsules; or intranasally such as, but not limited to, the form of powders, nasal drops or aerosols or certain agents; or transdermally such as not limited to a gel, ointment, lotion, suspension or patch delivery system with chemical enhancers such as dimethyl sulfoxide to either modify the skin structure or to increase the drug concentration in the transdermal patch (Junginger et al., in Drug Permeation Enhancement (Hsieh, ed., Marcel Dekker, Inc. NY, 1994)), or with oxidizing agents that enable the application of formulations containing proteins and peptides onto the skin (WO 98/53847), or applications of electric fields to create transient transport pathways such as electroporation, or to increase the mobility of charged drugs through the skin such as iontophoresis, or application of ultrasound such as sonophoresis (U.S. Pat. No. 4,309,989; U.S. Pat. No. 4,767,402)

For pulmonary administration, EBV-neutralizing antibody composition is delivered in a particle size effective for reaching the lower airways of the lung or sinuses. EBV-neutralizing antibody can be delivered by any of a variety of inhalation or nasal devices known in the art for administration of a therapeutic agent by inhalation. Various inhalers and dosage forms for antibody administration via inhalation are known in the art. See, e.g., U.S. Patent Pub. No. 2010/0129318.

Formulations for oral administration typically rely on the co-administration of adjuvants (e.g., resorcinols and nonionic surfactants such as polyoxyethylene oleyl ether and n-hexadecylpolyethylene ether) to increase artificially the permeability of the intestinal walls, as well as the co-administration of enzymatic inhibitors (e.g., pancreatic trypsin inhibitors, diisopropylfluorophosphate (DFF) and trasylol) to inhibit enzymatic degradation. The active constituent compound of the solid-type dosage form for oral administration can be mixed with at least one excipient, such as sucrose, lactose, cellulose, mannitol, gelatin, collagen, albumin, synthetic or semisynthetic polymers, or glyceride. These dosage forms can also contain other types of additives, e.g., inactive diluting agent, lubricant such as magnesium stearate, preserving agent such as sorbic acid, antioxidant such as cysteine, disintegrator, binder, thickener, buffering agent, sweetening agent, flavoring agent, perfuming agent, etc. Tablets and pills can be further processed into enteric-coated preparations. The liquid preparations for oral administration include emulsion, syrup, elixir, suspension and solution preparations allowable for medical use. These preparations can contain inactive diluting agents ordinarily used in said field, e.g., water. Liposomes and microspheres have been used to deliver pharmaceuticals. See, e.g., U.S. Patent Pub. No. 2010/0129318 (and references cited therein).

For absorption through mucosal surfaces, compositions and methods of administering EBV-neutralizing antibody include an emulsion comprising a plurality of submicron particles, a mucoadhesive macromolecule, a bioactive peptide, and an aqueous continuous phase, which promotes absorption through mucosal surfaces by achieving mucoadhesion of the emulsion particles. U.S. Pat. No. 5,514,670. Mucous surfaces suitable for application of the emulsions of the present invention can include corneal, conjunctival, buccal, sublingual, nasal, vaginal, pulmonary, stomachic, intestinal, and rectal routes of administration. Formulations for vaginal or rectal administration, e.g. suppositories, can contain as excipients, for example, polyalkyleneglycols, vaseline, cocoa butter, and the like. Formulations for intranasal administration can be solid and contain as excipients, for example, lactose or can be aqueous or oily solutions of nasal drops. For buccal administration excipients include sugars, calcium stearate, magnesium stearate, pregelinatined starch, and the like. U.S. Pat. No. 5,849,695.

For transdermal administration, the EBV-neutralizing antibody can be encapsulated in a delivery device such as a liposome or polymeric nanoparticles, microparticle, microcapsule, or microspheres (referred to collectively as microparticles unless otherwise stated). A number of suitable devices are known, including microparticles made of synthetic polymers such as polyhydroxy acids such as polylactic acid, polyglycolic acid and copolymers thereof, polyorthoesters, polyanhydrides, and polyphosphazenes, and natural polymers such as collagen, polyamino acids, albumin and other proteins, alginate and other polysaccharides, and combinations thereof. U.S. Pat. No. 5,814,599.

Sometimes, it is desirable to deliver the antibodies of the present invention to the subject over prolonged periods of time, for example, for periods of one week to one year from a single administration. Various slow release, depot or implant dosage forms can be utilized. For example, a dosage form can contain a pharmaceutically acceptable non-toxic salt of the compounds that has a low degree of solubility in body fluids, for example, (a) an acid addition salt with a polybasic acid such as phosphoric acid, sulfuric acid, citric acid, tartaric acid, tannic acid, pamoic acid, alginic acid, polyglutamic acid, naphthalene mono- or di-sulfonic acids, polygalacturonic acid, and the like; (b) a salt with a polyvalent metal cation such as zinc, calcium, bismuth, barium, magnesium, aluminum, copper, cobalt, nickel, cadmium and the like, or with an organic cation formed from, e.g., N,N'-dibenzyl-ethylenediamine or ethylenediamine; or (c) combinations of (a) and (b), for example, a zinc tannate salt. Additionally, the compounds of the present invention or, preferably, a relatively insoluble salt such as those just described, can be formulated in a gel, for example, an aluminum monostearate gel with, e.g. sesame oil, suitable for injection. Particularly preferred salts are zinc salts, zinc tannate salts, pamoate salts, and the like. Another type of slow release depot formulation for injection would contain the compound or salt dispersed for encapsulated in a slow degrading, non-toxic, non-antigenic polymer such as a polylactic acid/polyglycolic acid polymer for example as described in U.S. Pat. No. 3,773,919. The compounds or relatively insoluble salts such as those described herein can also be formulated in cholesterol matrix silastic pellets, particularly for use in animals. Additional slow release, depot or implant formulations, e.g. gas or liquid liposomes are known in the literature. See, e.g., U.S. Pat. No. 5,770,222; Sustained & Controlled Release Drug Deliv. Sys. (Robinson, ed., Marcel Dekker, Inc., NY, 1978).

An antibody of the present invention may form part of an immunotoxin. Immunotoxins are characterized by two components and are useful for killing selected cells in vitro or in vivo. One component is a cytotoxic agent which is usually fatal to a cell when attached or absorbed. The second component, known as the "delivery vehicle", provides a means for delivering the toxic agent to a particular cell type, such as cells comprising a carcinoma. The two components are commonly chemically bonded together by any of a variety of well-known chemical procedures. For example, when the cytotoxic agent is a protein and the second component is an intact immunoglobulin, the linkage may be by way of heterobifunctional cross-linkers, e.g., SPDP, carbodiimide, glutaraldehyde, or the like. Production of various immunotoxins is well-known with the art, and can be found, for example in Thorpe et al., Monoclonal Antibody: Toxin Conjugates. Aiming the Magic Bullet, in Monoclonal Antibodies in Clinical Med. 168 (Acad. Press, 1982).

A variety of cytotoxic agents are suitable for use in immunotoxins. Cytotoxic drugs interfere with critical cellular processes including DNA, RNA, and protein synthesis. Cytotoxic agents can include radionuclides, such as include 212Bi, 131I, 188Re, and 90Y; a number of chemotherapeutic drugs, such as vindesine, methotrexate, adriamycin, and cisplatin; and cytotoxic proteins such as ribosomal inhibiting proteins like pokeweed antiviral protein, Pseudomonas exotoxin A, ricin, diphtheria toxin, ricin A chain, etc., or an agent active at the cell surface, such as the phospholipase enzymes (e.g., phospholipase C). See generally, Olsnes & Phil, Chimeric Toxins, 25 Pharmac. Ther. 335-81 (1982); Monclonal Antibodies for Cancer Detection & Therapy, 159, 224 (Baldwin & Byers eds., Acad. Press, 1985).

The antibodies or peptides and derivatives can be used therapeutically as immunoconjugates. See Dillman, 111 Ann. Internal Med. 592-603 (1989). Such antibodies or polypeptides can be coupled to cytotoxic proteins, including, but not limited to ricin-A, Pseudomonas toxin and Diphtheria toxin. Toxins conjugated to antibodies or other ligands or peptides are well known in the art. See, e.g., Olsnes et al., 10 Immunol. Today 291 (1989). Plant and bacterial toxins typically kill cells by disrupting the protein synthetic machinery. Cytotoxic drugs that can be conjugated to anti-EBV antibodies and subsequently used for in vivo therapy include, but are not limited to, daunorubicin, doxorubicin, methotrexate, and Mitomycin C. For a description of these classes of drugs which are well known in the art, and their mechanisms of action, see Goodman & Gilman's Pharmacological Basis of Therapeutics (8th Ed., Macmillan Pub. Co., 1990). Additionally, the antibody of the present invention may be delivered in combination with chemotherapeutic agents such as oxaliplatin, irinotecan, topotecan, leucovorin, carmustine, vincristine, fluorouracil, streptozocin, and gemcitabine. Combinations of other antibodies and such compounds have been used in cancer patients. See, e.g., U.S. Patent Application Pub. No. 2002/0187144.

In an aspect of the present invention, the recombinant, humanized EBV-neutralizing antibody is administered to a subject suffering from X-linked lymphoproliferative disease (XLP). The antibody can be delivered over a period to time to prevent EBV infection, or to artificially restore effective balance to the subject's immune system such that immune responses can develop, al beit more slowly than in healthy individuals, while the administered antibody provides antibody that the subject does not produce endogenously. Additionally, because EBV is ubiquitous, the antibody of the present invention can be administered to the siblings of the XLP subject to minimize viral shed and risk of horizontal transmission to the XLP subject.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. A composition comprising a purified, recombinant, humanized EBV-neutralizing antibody.
2. The composition of paragraph 1, wherein the antibody has a heavy chain variable region selected from EVQLQQSGPELVKPGTSMKISCKASGSSFTDYTMNWMKQSHGKNLEWIGLINPYNGGT RYNQKFKGKATLTLDKSSSTAYMEVLSLTSEDSAVYYCAGGLRRVNWFAYWGQGTLV SVSA (SEQ ID NO:1) and DVQLVESGGGLVQPGGSRKLSCAASGFTFSSFGMHWVRQAPEKGLEWVAYISSGSSTLHYADTVKGRFTISRDNPKNTLFLQMTSLRSEDTAMYYCARWGNYPHYAMDYWGQGT SVTVSS (SEQ ID NO:2); and a variable light chain region selected from NIVMTQSPKSMSMSVGERVTLTCKASENVVTYVSWYQQKPEQSPKLLIYGASNRYTGVPDRFTGSGSATDFTLTISSVQAEDLADYHCGQGYSYPYTFGGGTKLEI (SEQ ID NO:3) and QAVLTQESALTTSPGETVTLTCRSSTGAVTTSNYANWVQEKPDHLFTGLIGGTNNRVPG VPARFSGSLIGDKAALTITGAQTEDEAIYFCVLWHSNHWVFGGGTKLTVL (SEQ ID NO:4); and said variable heavy and light chain regions are linked to human constant regions.
3. The composition of paragraph 2, wherein the heavy chain variable region has the amino acids EVQLQQSGPELVKPGTSMKISCKASGSSFTDYTMNWMKQSHGKNLEWIGLINPYNGGT RYNQKFKGKATLTLDKSSSTAYMEVLSLTSEDSAVYYCAGGLRRVNWFAYWGQGTLV SVSA (SEQ ID NO:1) and the light chain variable region has the amino acids QAVLTQESALTTSPGETVTLTCRSSTGAVTTSNYANWVQEKPDHLFTGLIGGTNNRVPG VPARFSGSLIGDKAALTITGAQTEDEAIYFCVLWHSNHWVFGGGTKLTVL (SEQ ID NO:4).
4. The composition of paragraph 1, wherein the purified, recombinant, humanized EBV-neutralizing antibody comprises human variable chain framework regions and the following CDRs:
CDR H1, GSSFTDYT (SEQ ID NO:5); CDR H2, INPYNGGT (SEQ ID NO:6); CDR H3, AGGLRRVNWFAY (SEQ ID NO:7);
CDR L1, TGAVTTSNY (SEQ ID NO:14); CDR L2, GTN (SEQ ID NO:15); and CDR L3, VLWHSNHWV (SEQ ID NO:16).
5. The use of the purified, recombinant, humanized EBV-neutralizing antibody of any one of the preceding paragraphs in a medicament for prophylactic treatment for preventing EBV-induced lymphoproliferative disease in immunosuppressed subjects.
6. The use of the purified, recombinant, humanized EBV-neutralizing antibody of any one of paragraphs 1 to 4 in a medicament to reduce the risk of B-lymphoproliferative disease in immunosuppressed subjects by maintaining a more equal balance between the expansion of EBV-infected B-cells and the weakened immune response.
7. The use of the purified, recombinant, humanized EBV-neutralizing antibody of any one of paragraphs 1 to 4 in a medicament to reduce the risk of infectious mononucleosis.
8. A method for preventing infectious mononucleosis in a subject suffering from genetic immunodeficiency comprising administering to the subject a pharmaceutical composition comprising a purified, recombinant, humanized EBV-neutralizing antibody.
9. The method of paragraph 8, wherein the purified, recombinant, humanized EBV-neutralizing antibody comprises the following CDRs:
CDR H1, GSSFTDYT (SEQ ID NO:5); CDR H2, INPYNGGT (SEQ ID NO:6); CDR H3, AGGLRRVNWFAY (SEQ ID NO:7);
CDR L1, TGAVTTSNY (SEQ ID NO:14); CDR L2, GTN (SEQ ID NO:15); and CDR L3, VLWHSNHWV (SEQ ID NO:16); wherein the CDRs are linked to human variable chain framework regions or human constant chain regions, or both of these.

10. An isolated nucleic acid encoding a CDR region selected from:
CDR H1, GSSFTDYT (SEQ ID NO:5); CDR H2, INPYNGGT (SEQ ID NO:6);
CDR H3, AGGLRRVNWFAY (SEQ ID NO:7); CDR L1, TGAVTTSNY (SEQ ID NO:14);
CDR L2, GTN (SEQ ID NO:15); and CDR L3, VLWHSN-HWV (SEQ ID NO:16).

11. The isolated nucleic acid of paragraph 10, wherein the nucleic acid is selected from the following:

```
CDR H1:                          (SEQ ID NO: 44)
GGNWSNWSNTTYACNGAYTAYACN;

CDR H2:                          (SEQ ID NO: 45)
ATHAAYCCNTAYAAYGGNGGNACN;

CDR H3:                          (SEQ ID NO: 46)
GCNGGNGGNYTNMGNMGNGTNAAYTGGTTYGCNTAY;

CDR L1:                          (SEQ ID NO: 47)
ACNGGNGCNGTNACNACNWSNAAYTAY;

CDR L2:                          (SEQ ID NO: 48)
GGNACNAAY;
and

CDR L3:                          (SEQ ID NO: 49)
GTNYTNTGGCAYWSNAAYCAYTGGGTN;
``` wherein N is A, T, C, or G; W is T or A; Y is C or T; and S is C or G.

12. An isolated nucleic acid encoding a purified, recombinant, humanized EBV-neutralizing antibody of any of paragraphs 1-4.

13. A composition comprising the antibody or nucleic acid of any of paragraph 1-4 and 10-12 and a pharmaceutically acceptable carrier.

14. The use of the isolated nucleic acid of any of paragraphs 10-13 in a medicament for prophylactic treatment for preventing EBV-induced lymphoproliferative disease in immunosuppressed subjects.

15. The use of isolated nucleic acid of any one of paragraphs 10-13 in a medicament to reduce the risk of B-lymphoproliferative disease in immunosuppressed subjects by maintaining a more equal balance between the expansion of EBV-infected B-cells and the weakened immune response.

16. The use of the isolated nucleic acid of any of paragraphs 10-13 in a medicament to reduce the risk of infectious mononucleosis.

17. A method for preventing infectious mononucleosis in a subject suffering from genetic immunodeficiency comprising administering to the subject a pharmaceutical composition comprising an isolated nucleic acid of any of paragraphs 10-13.

18. A method of producing an antibody comprising expressing the nucleic acid sequence of any of paragraphs 10-13.

EXAMPLES

Example 1

Molecular Cloning of Antibodies Expressed by Hybridomas Cell Line 72A1

The murine 72A1 hybridoma cell line was described originally as secreting a monoclonal antibody capable of neutralizing EBV infection. Hoffman et al., 77 PNAS 2979 (1980). Total RNA was isolated from 5 million cells 72A1 cells. Cells were washed twice at 4° C. with cold phosphate buffered saline (PBS), resuspended in 1 ml RNA-Bee-RNA isolation reagent (amsbio) and mixed with 0.2 ml chloroform. The suspension was centifuged at 15000 rpm for 15 min, 4° C. The upper RNA containing-phase was collected and mixed with the same volume of isopropanol. RNA was pelleted at 15000 rpm for 20 min, 4° C. and washed with 70% ethanol. Pellet was resuspended in 20 µl DEPC-treated water. Integrity of the isolated RNA was determined by standard acrylamide gel electrophoresis. (RNAse inhibitor, Applied Biosystems).

For single-strand cDNA synthesis, 1 µg of isolated RNA was denatured at 65° C. for 10 min, cooled and mixed with 0.5 µl DTT, 5 µl 5×RT-buffer, 0.5 µl RNasin (Applied Biosystems), 10 pmol cDNA synthesis-specific primers (m_IgG1, m_Kappa, m_Lambda 1-4 or m_Lambda 2-3), 250 µM of each dNTP, and 0.5 µl of the SuperScript II Reverse Transcriptase (Invitrogen), in a total volume of 25 µl. The reaction mix was incubated at 42° C. for 60 min, 52° C. for 30 min, and enzymes were inactivated by a 5 min incubation at 95° C. Excess primer was removed with a purifying column (Qiagen). To synthesize the polyA tail at the 5' end of the cDNA strand, 10 µl of the purified cDNA was mixed with 4 µl 5×TdT-buffer (Promega), 4 µl dATP (1 mM) and 0.3 µl (10 U) terminal deoxynucleotidyl transferase (TdT, Promega #M828A), total volume of 20 µl. The mix was incubated at 37° C. for 5 min and inactivated at 70° C. for 5 min. The volume of the reaction was adjusted to 0.5 ml.

PCR amplifications were performed with a forward primer (Poly-A-tail-5'), which hybridizes to the poly-A-tail added to the 5' end of the cDNA and a reverse primer, specific for the heavy or light chains (m_IgG1/2a, m_IgK long, m_IgL1, m_IgL2/3 long or m_IgL4). PCR was performed with two different DNA Polymerases: Deep Vent DNA Polymerase (BioLabs, #M0258S) and High Fidelity Platinum Taq DNA Polymerase (Invitrogen). For amplification with Deep Vent DNA Polymerase, using a 40 µl reaction mix, 10 µl of polyA-tailed cDNA was added to 4 µl of 10× Termal.Buffer, 250 µM each dNTP, 4 µM MgSO4, 0.2 µl Polymerase and 0.4 µM of each Primer. The reaction was incubated at 94° C. for 5 min, 57° C. for 5 min, 72° C. for 30 min; 40 cycles: 1 min 94° C., 30 sec 57° C., 2 min 72° C.; 10 min 72° C.; on ice. For amplification with High Fidelity Taq Polymerase, in a 40 µl reaction mix, 10 µl of polyA-tailed cDNA was added to 4 µl 10× Buffer, 4 µl 10× Enhancer, 250 µM each dNTP, 4 µM MgSO4, 0.2 µl Polymerase and 0.4 µM of each Primer. The reaction was incubated at 94° C. for 5 min, 57° C. for 5 min, 68° C. for 30 min; 40 cycles: 1 min 94° C., 30 sec 57° C., 2 min 68° C.; 10 min 68° C.; on ice.

For cloning into a TA vector, single bands were detected for mIgG1 (amplified with the Vent polymerase), and for mIgK and mIgL1 (both amplified with the High Fidelity Taq Polymerase) by standard gel electrophoresis. The bands were excised and purified (Qiagen Gel Extraction Kit) from 0.6% agarose gel. The purified products for mIgK and mIgL1 were cloned directly into a TOPO TA vector according to the manufacture's protocol (TOPO TA cloning kit, Invitrogen #45-0641). The PCR product for mIgG1 was incubated for 5 min at 72° C. with Taq Polymerase, because the product was synthesized with the Vent Polymerase which does not adds single deoxyadenosine (A) to the 3' ends of the PCR product. The sequences of the TA clones positive for mIgG1, mIgK or mIgL1, were revealed by sequencing with gene specific primers (m_IgG1/2a, m_IgK long or m_IgL1). Two different sequences were identified for mIgG1 (H1 and H2); 10 mIgG1 positive TA clones were sequenced, four had H1 sequence, six had H2 sequence.

Plasmids expressing humanized heavy and light chains from 72A1 cell line were generated as follows. Vectors expressing the constant region of human IgG1 (pCIRN) or the constant region of human IgK (pEIG) were provided (BIDMC, Boston, Mass.). Both sequences were confirmed by sequencing with Fc specific primers (for pCIRN: huIgG1 Fc f1, huIgG1 Fc r1, huIgG1 Fc r2; for pEIG: huIgK Fc f1, huIgK Fc r2). Both vectors were double digested with EcoRI and BsiWI.

The variable regions of both heavy (h1 and h2) and both light chains (k from mIgK and l from mIgL1) were amplified from the TA-clones, described above, by standard PCR with gene specific primers containing an EcoRI restriction side at the 5' end (forward primers: Vh1 EcoRI f, Vh2 EcoRI f, Vk EcoRI f and VL EcoRI 0 and BsiWI restriction side at the 3' end (reverse primers: Vh1 BsiWI r, Vh2 BsiWI r, Vk BsiWI r, VL BsiWI r). PCR products were digested with EcoRI for 2 hr at 37° C. and sequentially with BsiWI for 4 hr at 55° C. Digested PCR products were purified with QIAquick PCR purification kit (Qiagen) and ligated into the digested pCIRN (for h1 and h2) and pEIG (for k and l) according to the manufacture's protocol (T4 DNA ligase, BioLabs #M0202L). The correctness of the plasmids was confirmed by sequencing with Fc specific primers (for pCIRN: huIgG1 Fc r; for pEIG: huIgK Fc r2). Primers are shown in Table 1:

TABLE 1

Primers for cloning and characterization of EBV-neutralizing antibody

| Name | Sequence | SEQ ID NO: |
|---|---|---|
| RACE Primers | | |
| m_Kappa | CTC ATT CCT GTT GAA GCT GTT GAC | 21 |
| m_IgG1 | TAT GCA AGG CTT ACA ACC ACA | 22 |
| m_Lambda 2-3 | ACA CTC TGC AGG AGA CAG ACT CTT TTC | 23 |
| m_Lambda 1-4 | ACA CTC AGC ACG GGA CAA ACT CTT CTC | 24 |
| m_IgG1/2a | CAA TTT TCT TGT CCA CCT TGG TGC TGC | 25 |
| m_IgK long | CTC ATT CCT GTT GAA GCT CTT GAC AAT GGG | 26 |
| m_IgL1 | ACA CTC AGC ACG GGA CAA ACT CTT CTC CAC AGT | 27 |
| m_IgL2/3 long | ACA CTC TGC AGG AGA CAG ACT CTT TTC CAC AGT | 28 |
| m_IgL4 | ACA CTC AGC ACG GGA CAA ACT CTT CTC CAC AGT | 29 |
| Poly-A-tail-5" | GAC TCG AGT CGA CAT CGA TTT TTT TTT TTT TT | 30 |
| Cloning Primers | | |
| Vh1 EcoRI f | CAC TGA CTC GAA TTC ATG GGA TGG AGG TGG | 31 |
| Vh2 EcoRI f | CAC AGA CCA GAA TTC ATG GAC TCC AGG CTC | 32 |

TABLE 1-continued

Primers for cloning and characterization of EBV-neutralizing antibody

| Name | Sequence | SEQ ID NO: |
|---|---|---|
| Vh1 BsiWI r | GGT GTC GTC GTA CGT GCA GAG ACA GAG ACC | 33 |
| Vh2 BsiWI r | GGT GTC GTC GTA CGT GAG GAG ACG GTG AC | 34 |
| VL EcoRI f | CCT GGT TTG TGA ATT CAT GGC CTG GAT TTC AC | 35 |
| VL BsiWI r | GAC TTG GGC GTA CGT AGG ACA GTC AGT TTG G | 36 |
| Vk EcoRI f | CCA GCA TGG AAT TCA AGA TGG AAT CAC AGA C | 37 |
| Vk BsiWI r | GGT GCA GCA TCC GTA CGT TTT ATT TCC AGC | 38 |
| Sequencing Primers | | |
| huIgG1 Fc f1 | GGC AAG GAG TAC AAG TGC | 39 |
| huIgG1 Fc r1 | GCA CGG TCA CCA CGC TGC | 40 |
| huIgG1 Fc r2 | GGT GTA CAC CTG TGG TTC | 41 |
| huIgK Fc f1 | CGA ACT GTG GCT GCA CC | 42 |
| huIgK Fc r2 | CCT GAT GGG TGA CTT CG | 43 |

Expression and secretion of humanized 72A1 antibodies was carried out using HEK 293T cells, transiently transfected with any one of the four possible combinations of heavy and light chain vectors (Vh1+k, Vh1+l, Vh2+k, or Vh2+l). Transfection was performed with Effectine reagent (Invitrogen) according to the manufacture's protocol. Supernatants and cell lysates were collected 48 hr after transfection and analyzed by immunoblotting and ELISA for the presence of humanized 72A1 antibodies.

Multiple cDNAs for the immunoglobulins secreted by the 72A1 cells were obtained using rapid amplification of cDNA ends (RACE) on RNA isolated from the 72A1 cell line, with two different and unique sequences for a variable region linked to a murine IgG1 heavy chain sequence and multiple cDNAs with two different variable region sequences linked to the constant region for a kappa or a lambda light chain sequence. The cloning results suggested that the 72A1 cell line did not contain a single "monoclonal" antibody, but likely contained at least two different murine antibodies that could be derived from four different combinations of two heavy and two light chains. Thus, although the 72A1 cell line was reported to produce an antibody that reacts with EBV gp350 and an antibody that neutralizes EBV infection, the present work cast doubt whether both functions were mediated by the same antibody. Moreover, it was not known, before the present invention, which heavy and light chain combination mediated the reported functions.

The DNA sequence of the murine variable regions of both heavy and both light chains were cloned in-frame with the human immunoglobulin constant regions in order to express recombinant humanized forms of each murine immunoglobulin light and heavy chain. All four possible combinations of heavy and light chains were expressed by plasmid DNA transfection of eukaryotic cells.

Vh1 Variable Region (without Signal Sequence):

(SEQ ID NO: 1)
EVQLQQSGPELVKPGTSMKISCKASGSSFTDYTMNWMKQSHGKNLEWIGL

INPYNGGTRYNQKFKGKATLTLDKSSSTAYMEVLSLTSEDSAVYYCAGGL

RRVNWFAYWGQGTLVSVSA

Vh2 Variable Region (without Signal Sequence):

(SEQ ID NO: 2)
DVQLVESGGGLVQPGGSRKLSCAASGFTFSSFGMHWVRQAPEKGLEWVAY

ISSGSSTLHYADTVKGRFTISRDNPKNTLFLQMTSLRSEDTAMYYCARWG

NYPHYAMDYWGQGTSVTVSS

IgK Variable Region (without Signal Sequence):

(SEQ ID NO: 3)
NIVMTQSPKSMSMSVGERVTLTCKASENVVTYVSWYQQKPEQSPKLLIYG

ASNRYTGVPDRFTGSGSATDFTLTISSVQAEDLADYHCGQGYSYPYTFGG

GTKLEI

IgL Variable Region:

(SEQ ID NO: 4)
QAVLTQESALTTSPGETVTLTCRSSTGAVTTSNYANWVQEKPDHLFTGLI

GGTNNRVPGVPARFSGSLIGDKAALTITGAQTEDEAIYFCVLWHSNHWVF

GGGTKLTVL

Example 2

Immunological Characterization of 72A1 and Recombinant Antibodies

Figure 5:
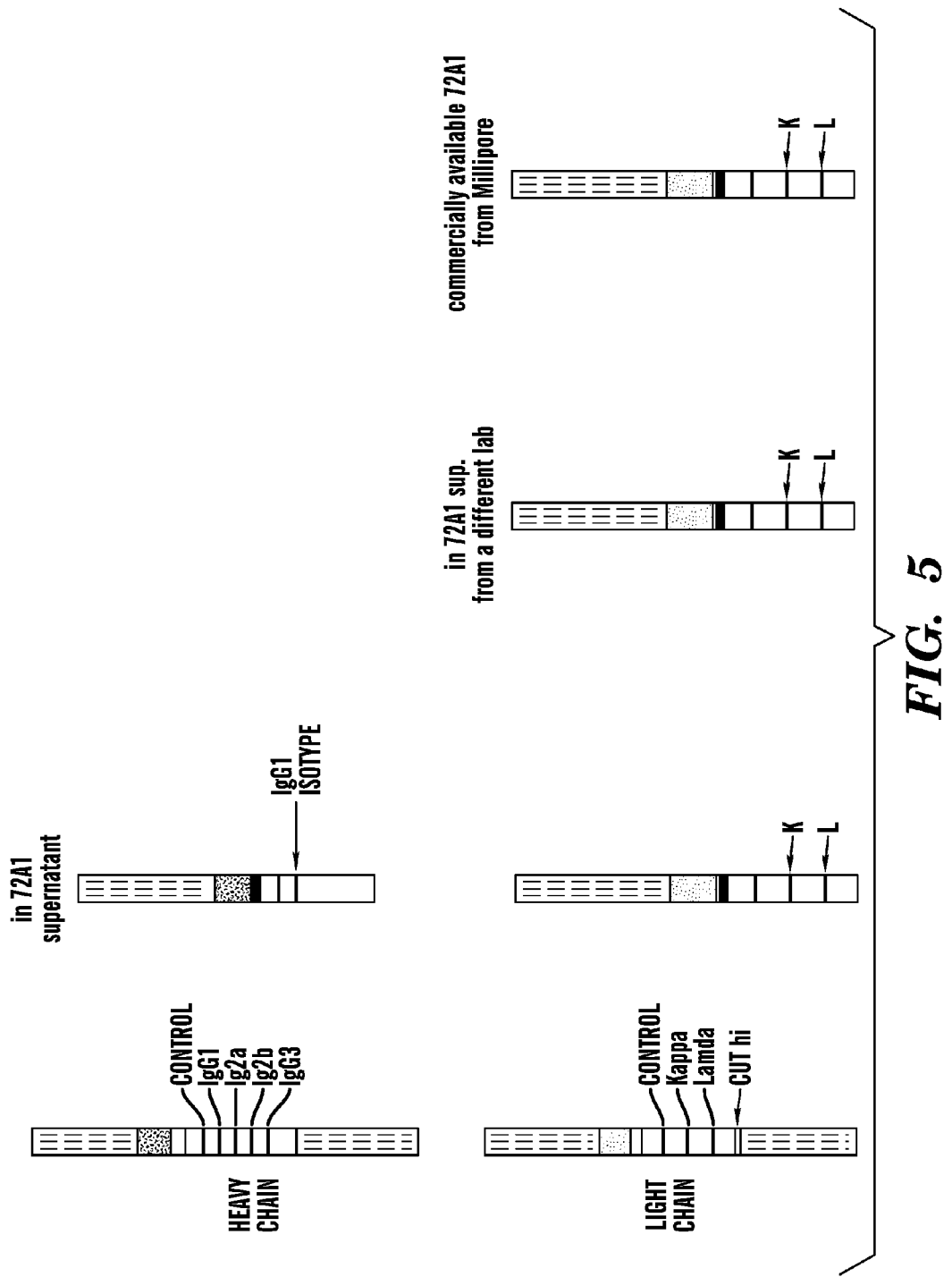
FIG. 5 shows data from immunoassays indicating that supernatants from various sources of 72A1 hybridoma cell lines contain both kappa and lambda light chains.

An immunoassay lateral flow device capable of detecting and differentiating murine kappa and lambda light chains was used to test 72A1 cell line supernatants and found evidence for both kappa and lambda light chains consistent with the cDNA cloning results. More specifically, supernatants from 72A1 cell line from a lab stock and also from an independent laboratory were collected and isotyped with IsoQuick Strips (Sigma) for IgG, IgK and IgL according to the manufacture's protocol. The same isotyping was also performed for a commercially available 72A1 antibody (Millipore #MAB10219) diluted 1:100 in PBS. Both kappa and lambda light chains were found in supernatants from both the earliest aliquots of 72A1 cells, from an independent sample obtained from a university laboratory (Louisiana State Univ., Shreveport), and from Millipore Corp. (Billerica, Mass.), as shown in FIG. 5. Phenotyping of 72A1 cell line by IgK and IgL staining was done as follows: Cells were washed once with cold PBS and surface stained with anti-mouse IgG (Jackson ImmunoResearch), anti-mouse IgK and anti-mouse IgL (SouthernBiotech) for 30 min at 4° C., according to the manufactures' protocols. Cells were washed twice with FACS wash buffer (PBS, 1% FCS, 0.1% sodium azide) and analyzed on a FACScalibur (BD Biosciences). Flow cytometry analysis indicated that 72A1 hybridoma cells were simultaneously expressing both kappa and lambda light chains. Evidence provided herein suggests that 72A1 was not, in fact, a monoclonal antibody.

All four possible combinations of heavy and light chains were recombined (i.e., Vh1+k, Vh1+L, Vh2+K, Vh2+L), expressed, and purified. Protein samples from HEK293T cell lysates and supernatants were separated by 15% SDS-PAGE and transferred to a nitrocellulose membrane. The blots were blocked for 1 hr at RT in 5% Milk-PBS-T (PBS with 1% Tween 20) and incubated with a HRP conjugated goat-anti-human IgG antibody (1:1000 dilution in 5% Milk-PBS-T). After intensive washing (3× with 5% Milk-PBS-T), the blot was developed with Western Lightning chemiluminescence reagent (Perkin Elmer).

For detection of EBV-specific and gp350 binding activity, purified EBV virions or column-purified EBV gp350 protein were diluted (1:100 or 1:50 respectively) in bicarbonate buffer (15 mM Na2CO3, 35 mM NaHCO3; pH 9.6) and 200 µl/well was incubated o.n. at 4° C. to coat a 96-well plate. The plate was washed three times with PBS-T and blocked with I-Block-PBS-T (0.3% I-Block (Applied Biosystems) in PBS with 0.1% Tween 20) for 2 hr at RT. Supernatants from transiently transfected HEK293Tcells, expressing H1L1, H1L2, H2L1, H2L2 or H1 and H2 alone, were diluted 1:2 in I-Block-PBS-T and 200 µl/well was incubated for 1 hr at RT. Human serum was diluted 1:50 and incubated at 200 µl/well. After intensive washing (thrice with PBS-T) the plate was incubated with a HRP-conjugated goat anti-human IgG antibody, diluted 1:1000 in I-Block-PBS-T at 200 µl/well for 1 hr at RT. The assay was measured for peroxidase activity after 30 min of incubation with O-phenylenediamine dihydrochloride (Sigma) at 450 nm using a Bio-Rad microplate reader. All specimens were tested in duplicate.

Competitive ELISA plates were coated with purified EBV gp350 and blocked as described herein. Supernatants from HEK293T cells were incubated for 1 hr at RT diluted in I-Block-PBS-T (dilutions as designated on the graph). After intensive washing (thrice with PBS-T) the plates were incubated with mouse 72A1 antibody, diluted 1:100 in I-Block-PBS-T at 200 µl/well for 1 hr at RT. Binding of the mouse antibody was detected with HRP-conjugated donkey-anti-mouse IgG antibody (1:1000 dilution in I-Block-PBS-T, 200 µl/well) incubated for 1 hr at RT.

For the EBV neutralizing assay, EBV (1 µl) was pre incubated at 37° C. with 20 µl of antibody-containing supernatant in a volume of 50 µl. After 1 hr, 2 million CFSE-labeled PBMC in a 50 µl volume were added to the virus and incubated for a further 90 min. Each sample was then transferred to a well of 24-well plate containing 2 mls of RPMI-10% FCS and cultured for 5 days. Cells were harvested, stained with anti-CD20 antibody to identify B cells, and analyzed for CFSE dilution on a FACSCalibur flow cytometer (BD Biosciences), data was analyses using FlowJo (Treestar). Labeled antibodies used were: Rat-anti-mouse Kappa, FITC conjugated (SouthernBiotech, No:1170-02,); Rat-anti-mouse Lambda, R-PE conjugated (SouthernBiotech, No:1175-09); Goat-anti-mouse IgG, FITC conjugated (Jackson ImmunoResearch, No: 115-095-003); Donkey-anti-mouse IgG (H+L), HRP conjugated (Jackson ImmunoResearch, No: 715-035-151); Goat-anti-human IgG (H+L), HRP conjugated (Jackson ImmunoResearch, No: 109-035-003)

Figure 6:
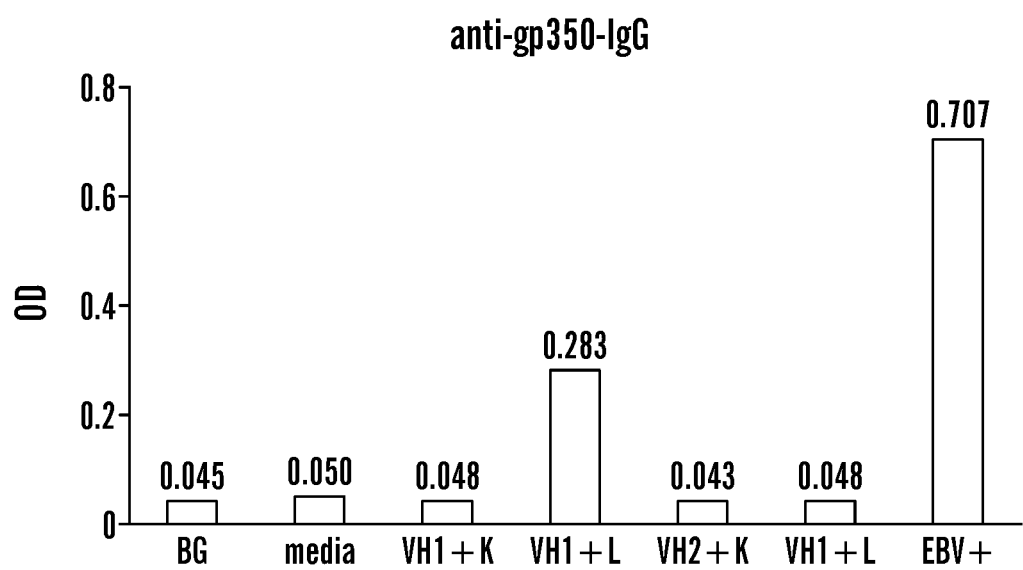
FIG. 6 is a bar graph reflecting the data from ELISA assays on the binding of recombinant antibodies having four different heavy and light chain combinations to EBV gp350. Antibody Vh1L bound to gp350.
Figure 7:
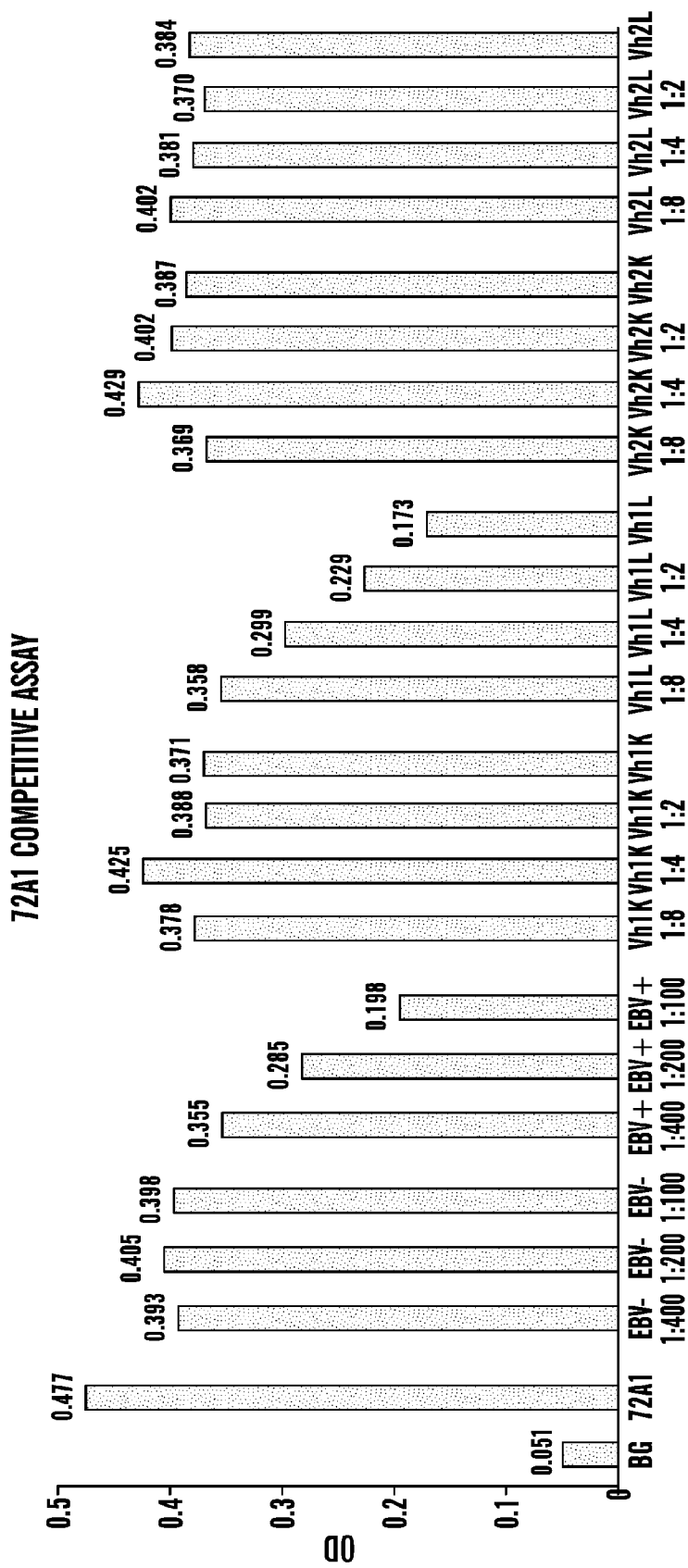
FIG. 7 is a bar graph showing data from competitive ELISA assays between antibodies derived from 72A1 hybridoma and four versions of heavy and light chain recombinant antibody constructs to EBV gp350. The recombinant antibody Vh1L competed with 72A1 for binding to gp350, indicating epitope identity.
Figure 8:
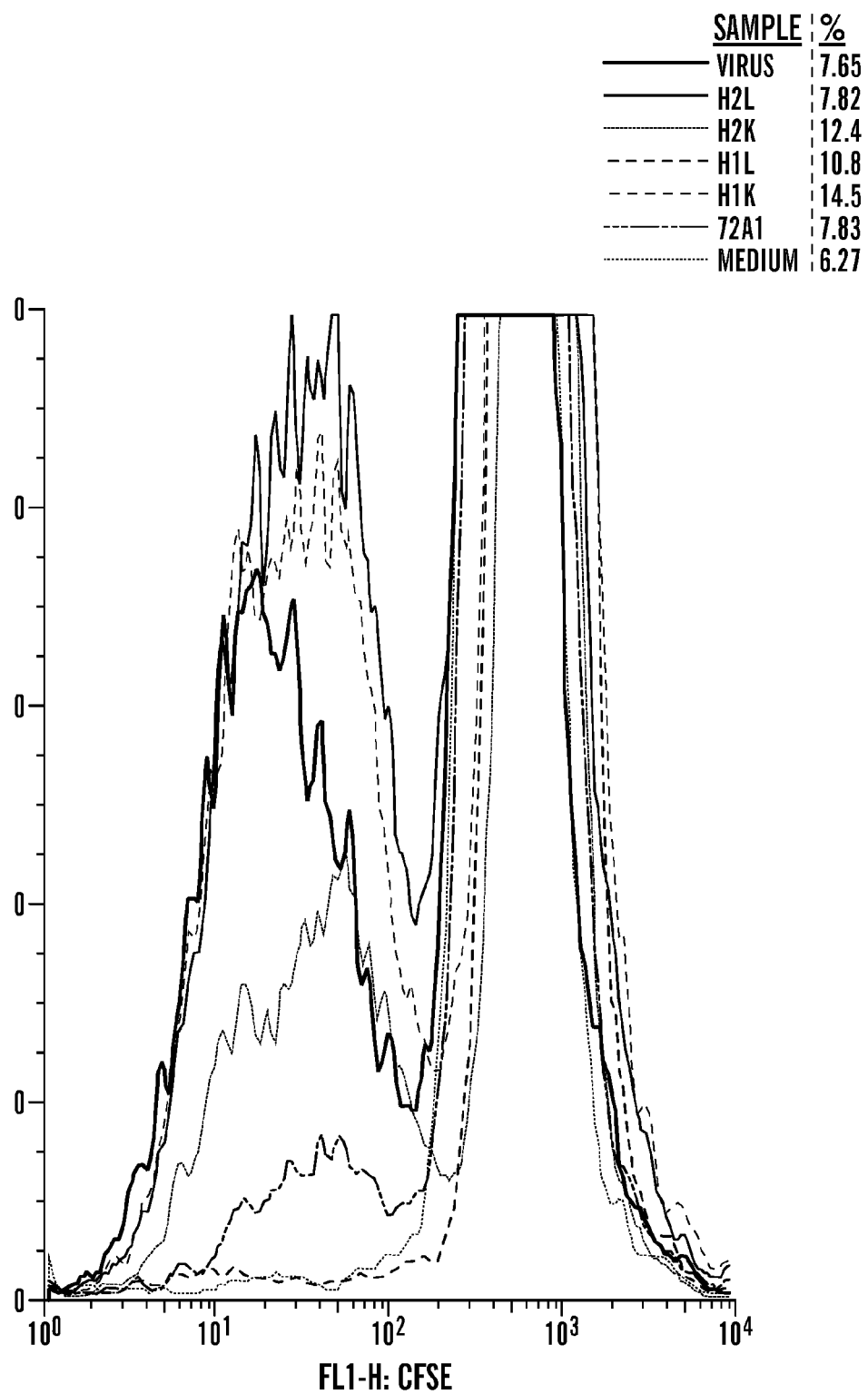
FIG. 8 shows data from neutralization assays; the data indicates that Vh1L neutralizes EBV. EBV was preincubated with supernatant from 293 transient tranfections, supernatant from 72A1, or medium alone. Virus was then cultured with CFSE labeled PBMC from 5 days. B-cells in PBMC were identified by CD20 staining and FACS analysis. The amount of B-cell division, identified by CFSE dilution was monitored, correlates with EBV infectivity. No CFSE dilution corresponds to EBV neutralization. Vh1L efficiently neutralized EBV infection to mock infection control levels, consistent with the Vh1L combination being responsible to EBV neutralizing activity in the 72A1 cell line. Supernatant form the 72A1 cell line also decreased CFSE dilution, indicating EBV neutralization. No other combinations significantly decreased EBV driven CFSE dilution and were thus not neutralizing.

Only one of the four combinations (designated "heavy chain 1 and lambda light chain;" Vh1 L) was found to bind gp350 by ELISA (FIG. 6), indicating that this combination is likely responsible for gp350 hinging in the original 72A1 cell line. This combination of heavy and light chain was also found to compete directly for gp350 binding with supernatants from the original 72A1 hybridoma, demonstrating binding to the same epitope. Moreover, a functional assay for EBV neutralization also demonstrated that this combination of heavy and light chain is responsible for neutralization activity.

The invention claimed is:

1. A composition comprising a purified, recombinant, humanized EBV-neutralizing antibody, wherein the antibody comprises the following CDRs:

| CDR H1, | GSSFTDYT; | (SEQ ID NO: 5) |
| CDR H2, | INPYNGGT; | (SEQ ID NO: 6) |
| CDR H3, | AGGLRRVNWFAY; | (SEQ ID NO: 7) |
| CDR L1, | TGAVTTSNY; | (SEQ ID NO: 14) |
| CDR L2, | GTN; and | (SEQ ID NO: 15) |
| CDR L3, | VLWHSNHWV. | (SEQ ID NO: 16) |

2. The composition of claim 1, wherein the antibody has a heavy chain variable region having the amino acids:

```
                                            (SEQ ID NO: 1)
EVQLQQSGPELVKPGTSMKISCKASGSSFTDYTMNWMKQSHGKNLEWIGL

INPYNGGTRYNQKFKGKATLTLDKSSSTAYMEVLSLTSEDSAVYYCAGGL

RRVNWFAYWGQGTLVSVSA
and
``` and a variable light chain region having the amino acids:

```
                                            (SEQ ID NO: 4)
QAVLTQESALTTSPGETVTLTCRSSTGAVTTSNYANWVQEKPDHLFTGLI

GGTNNRVPGVPARFSGSLIGDKAALTITGAQTEDEAIYFCVLWHSNHWVF

GGGTKLTVL;
``` and said variable heavy and light chain regions are linked to human constant regions.

3. The composition of claim 1, wherein the purified, recombinant, humanized EBV-neutralizing antibody comprises human variable chain framework regions and the following CDRs:

| CDR H1, | GSSFTDYT; | (SEQ ID NO: 5) |
| CDR H2, | INPYNGGT; | (SEQ ID NO: 6) |
| CDR H3, | AGGLRRVNWFAY; | (SEQ ID NO: 7) |
| CDR L1, | TGAVTTSNY; | (SEQ ID NO: 14) |
| CDR L2, | GTN; and | (SEQ ID NO: 15) |
| CDR L3, | VLWHSNHWV. | (SEQ ID NO: 16) |

4. A method for treating infectious mononucleosis in a subject suffering from genetic immunodeficiency comprising administering to the subject a pharmaceutical composition comprising a purified, recombinant, humanized EBV-neutralizing antibody of claim 1.

5. The method of claim 4, wherein the purified, recombinant, humanized EBV-neutralizing antibody comprises the following CDRs:

| CDR H1, | GSSFTDYT; | (SEQ ID NO: 5) |
| CDR H2, | INPYNGGT; | (SEQ ID NO: 6) |
| CDR H3, | AGGLRRVNWFAY; | (SEQ ID NO: 7) |
| CDR L1, | TGAVTTSNY; | (SEQ ID NO: 14) |
| CDR L2, | GTN; and | (SEQ ID NO: 15) |
| CDR L3, | VLWHSNHWV; | (SEQ ID NO: 16) | wherein the CDRs are linked to human variable chain framework regions or human constant chain regions, or both of these.

6. A method of treating EBV-induced lymphoproliferative disease in immunosuppressed subjects, the method comprising administering to the subject a pharmaceutical composition comprising a purified, recombinant, humanized EBV-neutralizing antibody of claim 1.

* * * * *